(12) United States Patent
Miras et al.

(10) Patent No.: US 7,741,073 B2
(45) Date of Patent: Jun. 22, 2010

(54) PLASTIDIAL TARGETING PEPTIDE

(75) Inventors: Stephane Miras, Lancey (FR); Daniel Salvi, Tullins (FR); Norbert Rolland, Saint-Egreve (FR); Jacques Joyard, Meylan (FR); Myriam Ferro, Fontaine (FR); Jerome Garin, Corenc (FR); Didier Grunwald, Saint-Egreve (FR)

(73) Assignee: Genoplante-Valor, Evry (FR)

( * ) Notice: Subject to any disclaimer, the term of this patent is extended or adjusted under 35 U.S.C. 154(b) by 0 days.

(21) Appl. No.: 12/103,174

(22) Filed: Apr. 15, 2008

(65) Prior Publication Data

US 2008/0263728 A1    Oct. 23, 2008

Related U.S. Application Data

(63) Continuation of application No. 10/517,309, filed as application No. PCT/FR03/01877 on Jun. 19, 2003, now Pat. No. 7,414,025.

(30) Foreign Application Priority Data

Jun. 21, 2002    (FR)    .................... 02 07729

(51) Int. Cl.
C12P 21/06    (2006.01)
C12N 1/20    (2006.01)
C12N 15/00    (2006.01)
C07H 21/02    (2006.01)

(52) U.S. Cl. ................ 435/69.1; 435/252.3; 435/320.1; 536/23.1

(58) Field of Classification Search ................ 536/23.1; 435/69.1, 320.1, 252.3
See application file for complete search history.

(56) References Cited

FOREIGN PATENT DOCUMENTS

| EP | 1033405 | 9/2000 |
| WO | 88/02402 | 4/1988 |
| WO | 02/10210 | 2/2002 |

OTHER PUBLICATIONS

Miras, Stephane, et al: "Non-canonical transit peptide for import into the chloroplast", Journal of Biological Chemistry, vol. 277, No. 49, pp. 47770-47778, Dec. 6, 2002.

Seigneurin-Berny, Dahne et al: "Differential extraction of hydrophobic proteins from chloroplast envelope membranes: A subcellular-specific proteomic approach to identify rare intrinsic membrane proteins." Plant Journal, vol. 19, No. 2, pp. 217-228, Jul. 1999.

Evan, M. et al: "Putative zinc-binding dehydrogenase from Arabidopsis" pp. 1-2, May 1, 2000.

*Primary Examiner*—Maryam Monshipouri
(74) *Attorney, Agent, or Firm*—Oblon, Spivak, McClelland, Maier & Neustadt, L.L.P.

(57) ABSTRACT

The invention relates to a non-cleavable, plastidial targeting polypeptide derived from a protein from the inner membrane of plant chloroplasts. Said peptide is particularly suitable for importing proteins of interest in plants.

17 Claims, 10 Drawing Sheets

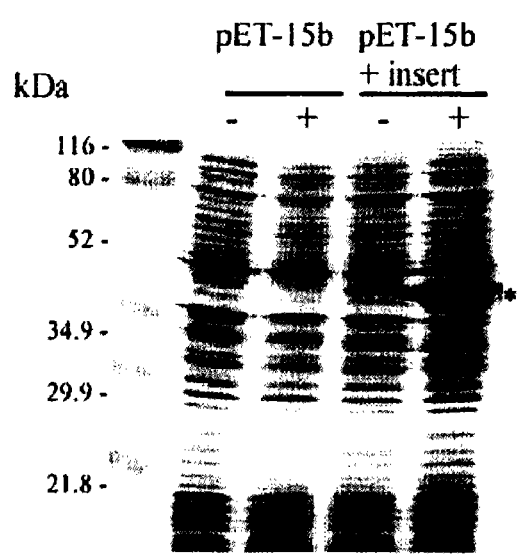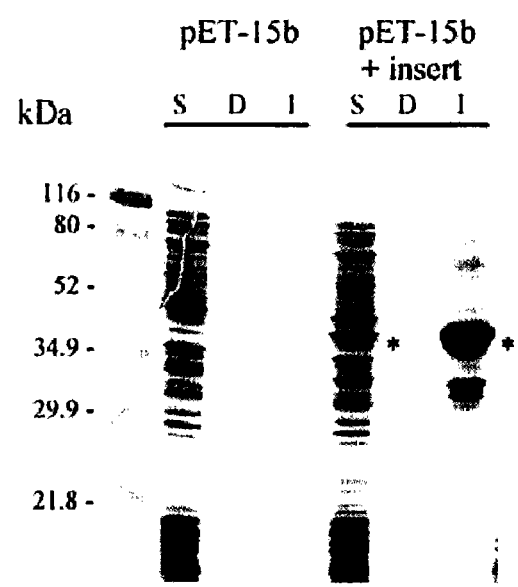
FIG. 1A
FIG. 1B

FIG. 3A
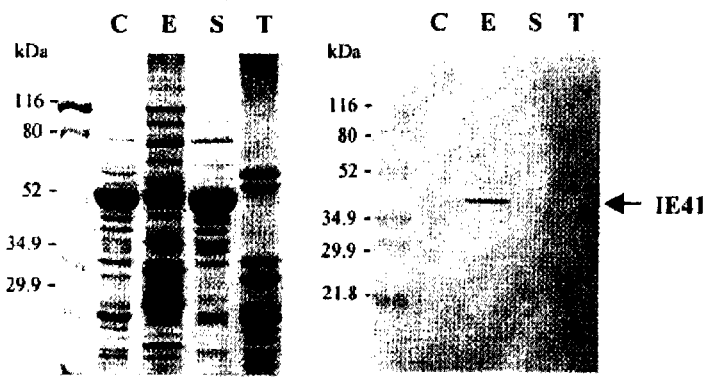
FIG. 3B
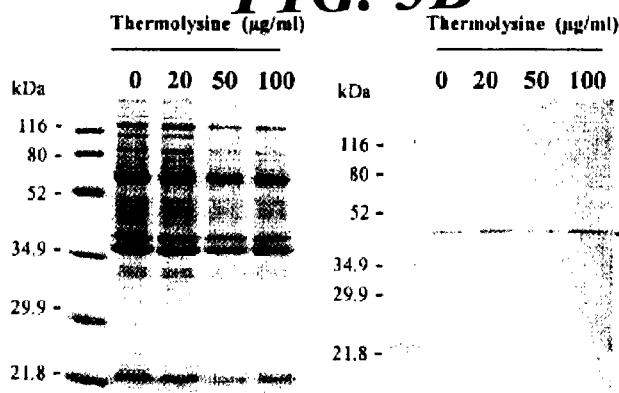
FIG. 3C
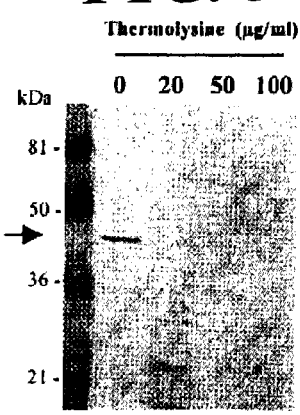
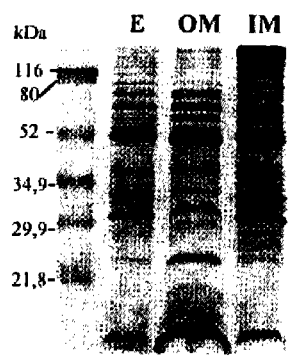 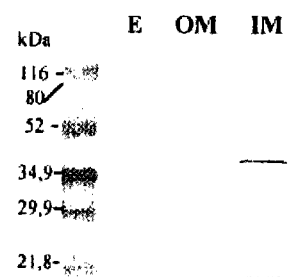 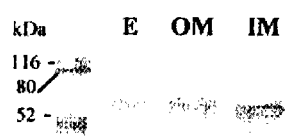
FIG. 3D

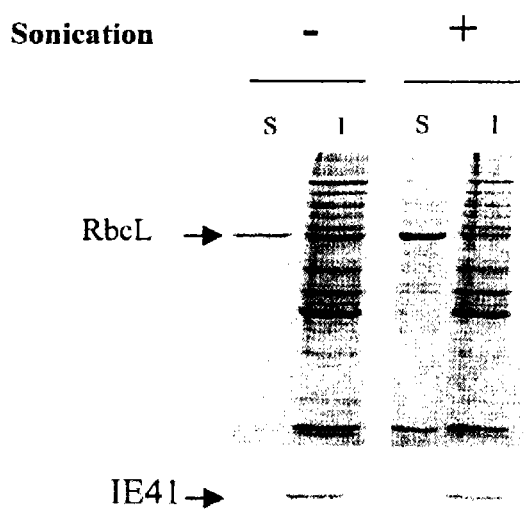
*FIG. 4A*
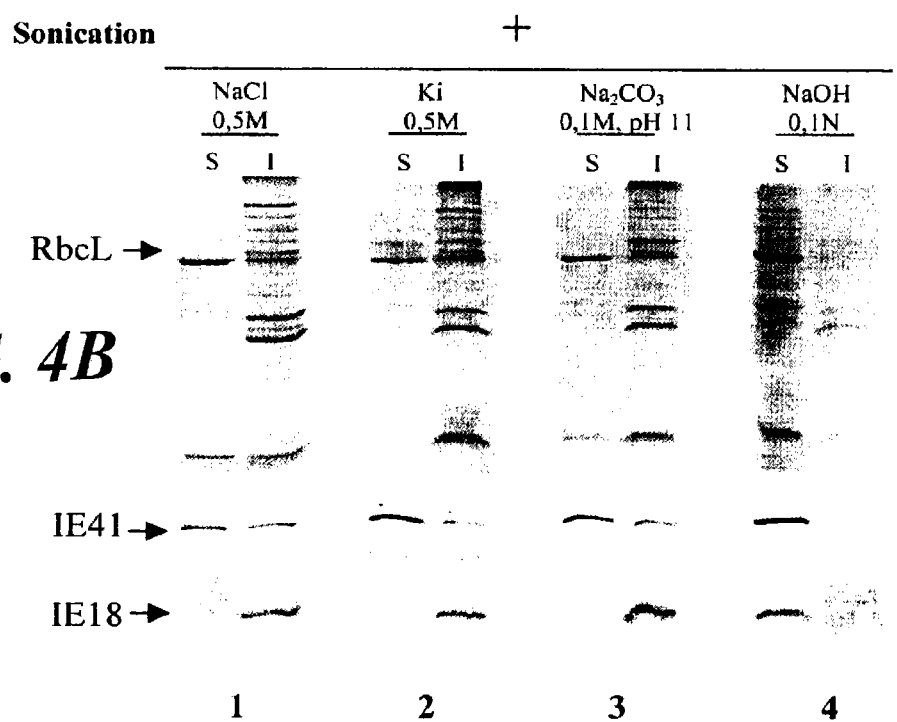
*FIG. 4B*
*FIG. 4C*

```
                                         ccatcctaata     8
cgactcactatagggctcgagcggccgcccgggcaggtcaaactgtggtaagataataca    68
gtaccattaccatctgacgcgcaaatggctgctaagctaatgcatgcgattcaatattct   128
                        M  A  A  K  L  M  H  A  I  Q  Y  S    12
ggctatggtggtggaactgatgctttaaagcatgttgaagttgctgttcctgatccaaag   188
 G  Y  G  G  T  D  A  L  K  H  V  E  V  A  V  P  D  P  K     32
tctgatgagttattgcttaaaattgaggctgcaactttgaacccaattgattggaagatt   248
 S  D  E  L  L  L  K  I  E  A  A  T  L  N  P  I  D  W  K  I   52
cagaaggGtgtacttcgtcccTcttaccccgcaagttccctactatacctggaactgat    308
 Q  K  G  V  L  R  P  L  L  P  R  K  F  P  T  I  P  G  T  D   72
gttgctggggaggtagtccaggctggatctgctgtaaataggtttaaaactggtgacaaa   368
 V  A  G  E  V  V  Q  G  S  A  V  N  R  F  K  T  G  D  K     92
gtcgtggccgtgcttagtcatgctactgggggtgcactagctgaatatgccgtggcgaag   428
 V  V  A  V  L  S  H  A  T  G  G  A  L  A  E  Y  A  V  A  K  112
gagaacctgacagttgctagaccaccagaagtatcagcagcagaaggtgctgccttacct   488
 E  N  L  T  V  A  R  P  P  E  V  S  A  A  E  G  A  A  L  P  132
gttgctgccctcacggctcaccaagctctcacccagtttgccaacatcaagctcgatgga   548
 V  A  A  L  T  A  H  Q  A  L  T  Q  F  A  N  I  K  L  D  G  152
agtggtgaaaggaagaacatattgatcacggctgcatcagggggtgtgggccactatgcg   608
 S  G  E  R  K  N  I  L  I  T  A  A  S  G  G  V  G  H  Y  A  172
gtccagctggcaaagctcgggaacacgcatgtaacagcaacatgtggagcccgcaaccta   668
 V  Q  L  A  K  L  G  N  T  H  V  T  A  T  C  G  A  R  N  L  192
gatttcgtgaaaggcttgggtgccgatgaggttcttgactacaaaacacctgaaggggcg   728
 D  F  V  K  G  L  G  A  D  E  V  L  D  Y  K  T  P  E  G  A  212
tccttgacaagcccgtcaggaaagaaatatgactacgtagtccacggtgcaagcggaatc   788
 S  L  T  S  P  S  G  K  K  Y  D  Y  V  V  H  G  A  S  G  I  232
ccttggtccacctttgagcccaatttgagtgaagcaggtaaggtaatagatttgactcct   848
 P  W  S  T  F  E  P  N  L  S  E  A  G  K  V  I  D  L  T  P  252
ggcccaactgcaatgatgacatttgcttggaaaaagctaacattctccaaaaagcagctg   908
 G  P  T  A  M  M  T  F  A  W  K  K  L  T  F  S  K  K  Q  L  272
gtgcctctgcttttgataccaaagatccccaactttgaatatgttgtgaatttggtaaag   968
 V  P  L  L  L  I  P  K  I  P  N  F  E  Y  V  V  N  L  V  K  292
gaaaagaagcttaaaacagtcatagactctaaacatcccttgagtaaaggtgaagatgct  1028
 E  K  K  L  K  T  V  I  D  S  K  H  P  L  S  K  G  E  D  A  312
tggagtaggataatgggtggtcatgctacagggaagattataatcgagccttgaatagaa  1088
 W  S  R  I  M  G  G  H  A  T  G  K  I  I  I  E  P  *        329
aatattgatgcagacccgctatatattgcttgaaggttacaaactttTaagtttatagta  1148
cttgagttatactttcctagttgtaaacattcaagtatttcataatgttatactttccta  1208
gtttcctccaaaaaaaa                                             1225
```

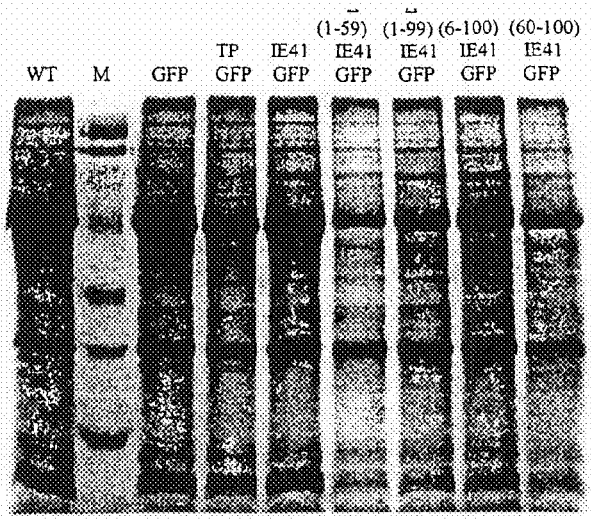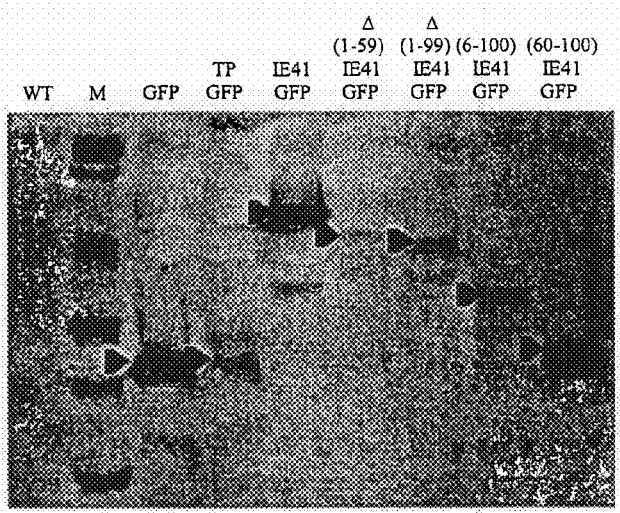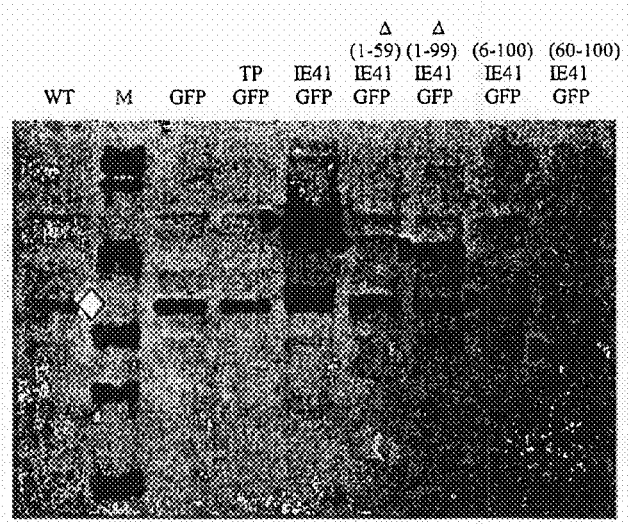
Fig. 9

PLASTIDIAL TARGETING PEPTIDE

CROSS-REFERENCE TO RELATED APPLICATIONS

This application is a continuation of U.S. application Ser. No. 10/517,309 filed Aug. 3, 2005, now U.S. Pat. No. 7,414,025, which is a 371 application of PCT/FR03/01877 filed Jun. 19, 2003 and claims the benefit of FR02/07729 filed Jun. 21, 2002.

FIELD OF THE INVENTION

The present invention relates to the production of proteins of interest in plants, and in particular to the targeting thereof to the plastid compartment.

BACKGROUND OF THE INVENTION

Plasts are intracellular organelle of chlorophyll-containing plants (algae, mosses, and higher plants). Several main types of plasts can be distinguished according to their pigment content and the nature thereof: amyloplasts, which are rich in starch, chloroplasts in which the main pigments are chlorophylls, and chromoplasts for which the main pigments are keratonoids. These three categories of plasts which derive from common precursors, proplasts, have a common basic structure consisting of a double membrane enclosing the plastid stroma. In chloroplasts, there is a third membrane system forming, within the stroma, saccules called thylakoids.

Besides their essential role in photosynthesis, chloroplasts are also involved in redox reactions, for example the reduction of nitrates to ammonium. Plasts also play an essential role in the biosynthesis and/or the storage of many molecules, among which mention will be made of starch, lipids, carotenoids, most amino acids, plant hormones (abscissic acid, precursors of gibberellins, jasmonate, etc.).

Although plasts have their own genome encoding some of their proteins, a large number of the enzymes involved in the various plastid functions are encoded by the nuclear genome and imported into the plasts.

This importation is carried out via a specific mechanism, which has more particularly been studied in the case of chloroplasts (for review cf. CHEN and SCHNELL, Trends Cell Biol. 9, 222-227, 1999; KEEGSTRA and CLINE, The Plant Cell 11, 557-570, 1999; SCHLEIFF and SOLL, Planta 211, 449-456, 2000; JACKSON-CONSTAN and KEEGSTRA, Plant Physiol. 125, 1567-1676, 2001). This mechanism involves an import system in each of the two plastid membranes: in the outer membrane, the Toc (translocon at outer membrane of chloroplast) complex which comprises at least three proteins: Toc 86, 75 and 34 (KESSLER et al., Science 266, 1035-1039, 1994; PERRY and KEEGSTRA, Plant Cell 6, 93-105, 1994); in the inner membrane, the Tic (translocon at inner membrane of chloroplast) complex which comprises at least four proteins: Tic 110, 55, 22 and 20 (KESSLER and BLOBEL, Proc. Natl. Acad. Sci. 93, 7684-7689, 1996; LÜBECK et al., EMBO J. 15, 4230-4238, 1996; CALIEBE et al., EMBO J. 16, 7342-7350, 1997; KOURANOV et al., J. Cell Biol., 143, 991-1002, 1998), and also a chaperone protein in the stroma: ClpC (AKITA et al., J. Cell Biol. 136, 983-994, 1997; NIELSEN et al., EMBO J. 16, 935-946, 1997).

A major element of this mechanism is Toc75, which is the most abundant protein in the outer membrane, and forms the central pore of the translocation channel located in this membrane (SCHNELL et al., Science 266, 1007-1012, 1994; TRANEL et al., EMBO J. 14, 2436-2446, 1995). Toc75 interacts specifically with a particular sequence, called "targeting peptide" or "transit peptide", located at the N-terminal end of the proteins imported into the plasts (MA et al., J. Cell Biol. 134, 315-327, 1996).

Many targeting peptides have been identified in the precursors of proteins targeted to the intermembrane space, the inner membrane, the stroma and, in the case of chloroplasts, to the thylakoid membrane.

Among the proteins known to have a cleavable intraplastid-targeting peptide, mention will in particular be made of proteins targeted to the intermembrane space (Tic22: KOURANOV et al., 1998, mentioned above; KOURANOV et al., J. Biol. Chem. 274, 25181-25194, 1999), proteins targeted to the inner membrane (TPT(Triose-Pi/Pi translocator): BRINK et al., J. Biol. Chem. 270, 20808-20815, 1995), proteins targeted to the stroma (ribulose-1,5-bisphosphate carboxylase (Rubisco) small subunit): DE CASTRO SILVA FILHO et al., Plant Mol. Biol. 30, 769-780, 1996; carbonic anhydrase), proteins targeted to the thylakoid membrane (LHCP (light harvesting complex): LAMPPA et al., J. Biol. Chem. 263, 14996-14999, 1988; Cfo-II: ATPase subunit) and to the thylakoid lumen (OEE1 (Oxygen Evolving Element 1): KO and CASHMORE, EMBO J. 8, 3187-3194, 1989).

These targeting peptides generally comprise between 40 and 100 amino acids, and most of them have common characteristics: they are virtually devoid of negatively charged amino acids, such as aspartic acid, glutamic acid, asparagine or glutamine; their N-terminal region is devoid of charged amino acids, and of amino acids such as glycine or proline; their central region contains a very high proportion of basic or hydroxylated amino acids, such as serine or threonine; their C-terminal region is rich in arginine and has the ability to form an amphipathic, beta-sheet secondary structure.

In the case of proteins targeted to the thylakoid lumen, the targeting peptide is bipartite and comprises additional information for crossing the thylakoid membrane (DE BOER and WEISBEEK, Biochim. Biophys. Acta. 1071, 221-253, 1991). In certain cases, this bipartite targeting peptide can also be found in proteins targeted to the thylakoid membrane (KARNAUCHOV et al., J. Biol. Chem. 269, 32871-32878, 1994).

In all cases, the targeting peptide is cleaved after importation. This cleavage is carried out by specific proteases; a protease located in the stroma (VANDERVERE et al., Proc. Natl. Acad. Sci. 92, 7177-7181, 1995), and a protease located in the lumen of the thylakoid (CHAAL et al., J. Biol. Chem. 273, 689-692, 1998) have been described.

Proteins targeted to the outer membrane do not generally comprise a cleavable signal peptide; the targeting information is contained in the mature protein (CLINE and HENRY, Annu. Rev. Cell Dev. Biol., 12, 1-26, 1996); after they have been synthesized in the cytosol, these proteins are directly incorporated into the membrane (VAN'T HOF et al, FEBS lett. 291, 350-354, 1991 and J. Biol. Chem. 268, 4037-4042, 1993; PINADUWAGE and BRUCE, J. Biol. Chem. 271, 32907-32915, 1996) by means of interactions, the nature of which remains poorly understood, with the lipid bilayer. The only known exception to date concerns the Toc75 protein or (OEP75), the targeting of which to the outer membrane requires the presence of a cleavable, bipartite N-terminal targeting peptide (TRANEL et al., 1995, mentioned above; TRANEL and KEEGSTRA, Plant Cell 8, 2093-2104, 1996).

It is known that the use of plast-targeting peptides is necessary for introducing into these plasts proteins of interest for acting on various plastid functions, in particular with the aim of improving the characteristics of plants of agronomic interest, for example the biosynthesis of lipids, of starch, of vitamins, of hormones or of proteins by said plants, or their resistance to diseases, to insects or to herbicides. For example, application EP 189707 proposes the use of cleavable targeting peptides derived from chloroplast protein precursors, and in particular of the ribulose-1, 5-bisphosphate carboxylase small subunit targeting peptide, for importing a protein of interest into chloroplasts; PCT application WO 00/12732 proposes the use of targeting peptides from various plastid proteins, for importing proteins of interest into plasts.

The plastid functions can be modified in this way, and the characteristics conferred by these modifications are very diverse.

For the purposes of nonlimiting illustration, mention may be made of:

an increase in herbicide resistance, by expression of the precursor of acetolactate synthetase (ALS), (LEE et al. EMBO J., 7, 1241-1248, 1988), of mutated acetolactate synthetase (PRESTON and POWLES, Heredity 88, 8-13, 2002); CHONG and CHOI, Biochem. Biophys. Res. Commun. 279, 462-467, 2000), or of 3-enolpyruvylshikimate-5-phosphate synthetase (EPSP synthetase) (KLEE et al., Mol. Gen. Genet., 210, 437-442, 1987);

an increase in resistance to various stresses, by expression of zeaxanthin epoxidase, (SEO et al., Trends Plant Sci., 7, 41-48, 2002), of choline monooxygenase (SHEN et al., Sheng Wu Gong Cheng Xue Bao, 17, 1-6, 2001), of the product of the ERD1_ARATH gene (KIYOSUE et al., Biochem. Biophys. Res. Commun., 15, 196, 1214-1220, 1993), of ferrochelatase (CHOW et al., J. Biol. Chem., 31, 272, 27565-27571, 1997), of omega −3 fatty acid desaturase (IBA et al., Tanpakushitsu Kakusan Koso, 39, 2803-2813, 1994; MURAKAMI et al., Science 21, 287(5452), 476-479, 2000), or glutamine synthetase (FUENTES et al., J. Exp. Bot., 52, 1071-1081, 2001);

modification of plast metabolism, so as to increase the capture of light energy (GAUBIER et al., Mol. Gen. Genet., 1, 249, 58-64, 1995), the photosynthetic and growth capacities (MIYAGAWA et al., Nature Biotech., 19, 965-969, 2001), the carotenoid content (HUGUENEY et al., Eur. J. Biochem., 1, 209, 399-407, 1992; MANN et al., Nature Biotech., 18, 888-892, 2000), or the content of various substances of interest, such as starch (PCT application WO 00/11144), essential amino acids (MUEHLBAUER et al., Plant Physiol., 106, 1303-1312, 1994), provitamin A (RÖMER et al., Nature Biotech., 18, 666-669, 2000), hormones (JO-YARD et al., Plant Physiol. 118, 715-723, 1998), etc.;

overexpression and chloroplast-targeting of proteins that can be used for the purposes of bioremediation (detoxification or depollution of contaminated soils), such as ferritin, (LOBREAUX et al., Biochem. J., 15, 288(Pt 3), 931-939, 1992), proteins of the phytochelatin family (CAZALE and CLEMENS, FEBS 507, 215-219, 2001 ; TSUJI et al., BBRC 293, 653-659, 2002), etc.

All the intraplastid-targeting peptides known in the prior art make it possible to import a protein into plasts by means of the TOC and TIC membrane import systems, as indicated above. It has been noted that the use of these peptides for targeting proteins of interest into chloroplasts may, in particular when the targeting peptide/protein of interest construct is placed under control of a strong promoter such as the 35S promoter, has the drawback of saturating these import systems, by competing with the proteins naturally targeted to the chloroplast. As a result of this, "leakages" occur, resulting, after a few days, in the presence of the protein of interest in other subcellular compartments such as the cytoplasm.

It would be desirable to have intraplastid-targeting peptides which would not depend on the TOC/TIC import system and would therefore make it possible to avoid the abovementioned drawbacks.

In previous studies aimed at identifying, by means of a proteomic approach, proteins from spinach chloroplast membrane preparations, the inventors identified, inter alia, peptides having considerable sequence similarity with a putative 41 kDa protein from *Arabidopsis* (TrEMBL accession number Q9SV68) (SEIGNEURIN-BERNY et al., Plant. J. 19, 217-228, 1999; FERRO et al., Electrophoresis 21, 3517-3526, 2000).

SUMMARY OF THE INVENTION

In continuing their studies in order to more fully characterize the *Arabidopsis* protein, and its homologue in spinach, the inventors noted that, surprisingly, although this involves proteins synthesized in the cytoplasm and imported at the inner membrane of the chloroplast, the importation thereof was carried out without cleavage of a targeting peptide; in addition, sequence analysis of these proteins reveals no sequence having the characteristics of known plastid-targeting peptides.

BRIEF DESCRIPTION OF THE DRAWINGS

FIG. 1:

A. Expression experiments in Example 1 are shown where after induction with IPTG, the recombinant protein is strongly expressed in the bacteria transformed with the plasmid pET-15b containing the *Arabidopsis* cDNA insert.

pET-15b =bacteria transformed with the nonrecombinant plasmid (negative control) pET-15b+insert=bacteria transformed with the recombinant plasmid, −=no induction with IPTG, +=induction with IPTG,

*= band corresponding to the recombinant 41 kDa protein.

B. Solubilization of the Recombinant Protein in Example 1 is shown where the recombinant protein (*) is found in 2 different fractions: a water-soluble fraction present in the *E. coli* cytosol and an insoluble fraction, which is not solubilized by Triton X-100, which indicates that it is probably aggregated in the form of inclusion bodies:

pET–15b=bacteria transformed with the nonrecombinant plasmid (negative control), pET–15b+insert=bacteria transformed with the recombinant plasmid, S=soluble proteins, D=proteins solubilized in Triton X-100, I=proteins not solubilized in Triton X-100,

*=band corresponding to the recombinant 41 kDa protein.

Figure 2:
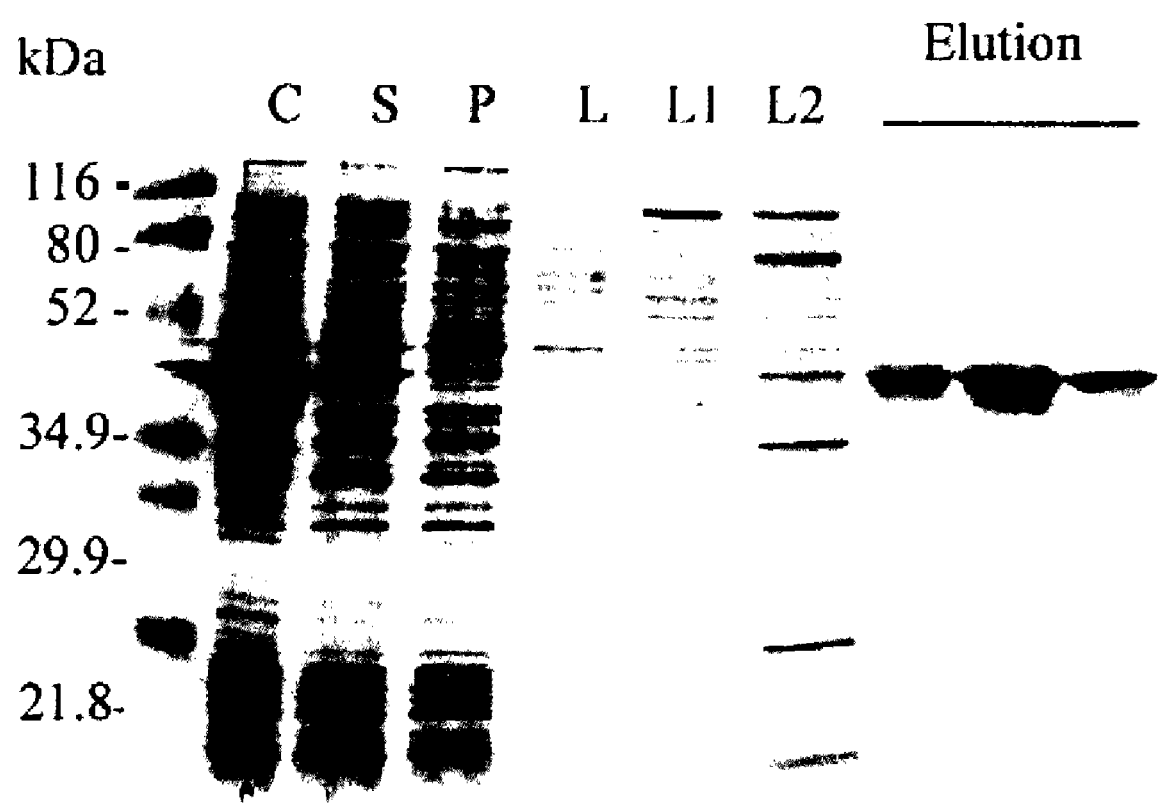

FIG. 2: Purification of the Recombinant Protein in Example 1 is shown:

C=bacterial pellet diluted in the lysis buffer (10 μl,

S=soluble bacterial proteins (10 μl ),

P=proteins not bound (10 μl),

L, L1, L2=washes with the lysis buffer (35 and 60 mM imidazole) (15 μl),

Elution=fraction eluted in the presence of 250 mM imidazole.

FIG. 3: Analysis of the Chloroplast Fractions in Example 1 is shown:

A. The 41 kDa protein is associated only with the chloroplast envelope and is not detected in the stroma or in the thylakoids.

C=chloroplast proteins,
E=envelope membrane proteins,
S=stroma proteins,
T=thylakoid membrane proteins.

B, C The 41 kDa protein is not affected by the treatment with thermolysin (FIG. 3B), whereas the same proteolytic treatment carried out on solubilized envelope proteins shows the sensitivity of the 41 kDa protein to the thermolysin treatment (FIG. 3C).

0=absence of thermolysin,
20=thermolysin at 20 µg/ml,
50=thermolysin at 50 µg/ml,
100=thermolysin at 100 µg/ml.

D. The 41 kDa protein is found, like the IE18 protein, only in the preparations of chloroplast envelopes enriched in inner membrane.

E=envelope membrane proteins,
OM=outer membrane proteins,
IM=inner membrane proteins.

FIG. 4 Analysis of the Interactions Between the IE41 Protein and the Inner Membrane of the Chloroplast Envelope A. The analyses by SDS-PAGE and Western blotting of the treated envelope fractions show that the IE41 protein is not solubilized after sonication of the envelope vesicules. On the contrary, the major soluble proteins of the stroma (RbcL) which are sequestred in the envelope vesicules, and which are known to contaminate the envelope fractions, are solubilized by this treatment. This shows that the IE41 protein is neither a soluble protein of the intermembrane space, nor a soluble protein of the stroma that contaminates the purified envelope fraction.

−=no sonication,
+=sonication,
S=soluble proteins, I=membrane proteins.

B. These results show that the IE41 protein is at least partly solubilized by the salt (KI, NaCl) or moderately alkaline (Na$_2$CO$_3$) treatments, which have no effect on the intrinsic protein IE18, it only being possible for the latter to be solubilized by a strong alkaline treatment (NaOH).

+=sonication (10 sec),
NaCl 0.5 M=treatment 1,
KI 0.5 M=treatment 2,
0.1 M Na$_2$CO$_3$,
pH 11=treatment 3,
0.1 N NaOH=treatment 4,
S=soluble protein fraction,
I=insoluble protein fraction.

C. These results show that the IE41 protein can be completely solubilized with concentrations of Triton X-100 (0.2%) that are much lower than those (of the order of 2%) which are necessary for solubilizing the intrinsic proteins.

Mix=purified envelope vesicules,
M=envelope membrane proteins,
S=envelope soluble proteins.

Figures 5A, 5B:
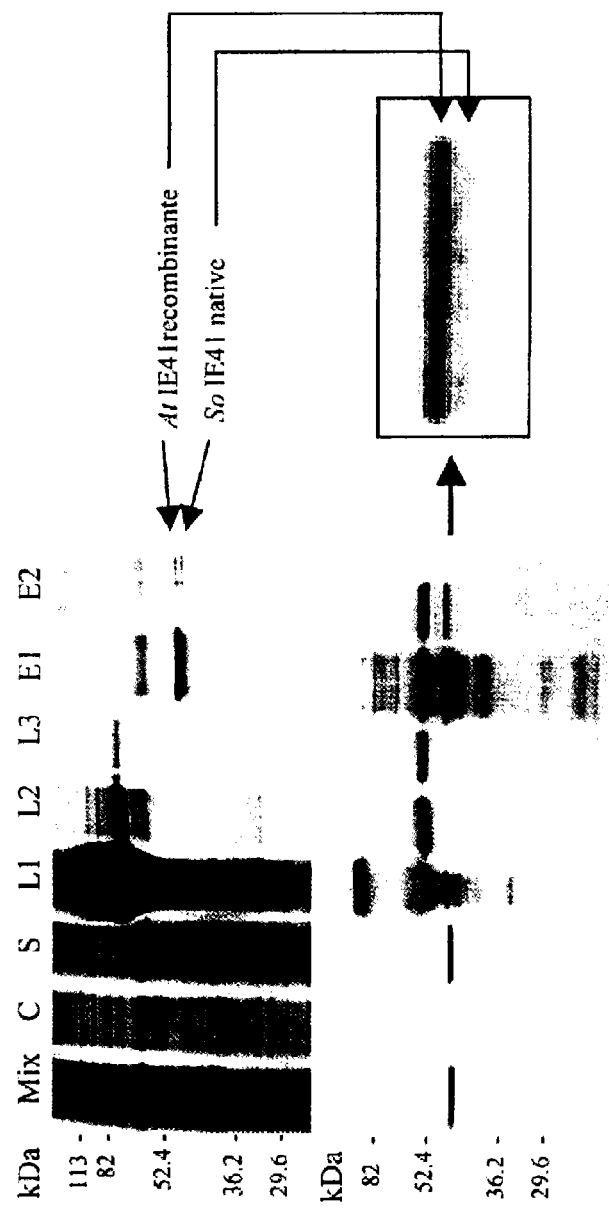

FIG. 5: Immunopurification of the Spinach IE41 Protein. The E2 fraction comprising the purified natural spinach IE41 protein (So) remains contaminated by the recombinant *Arabidopsis* (His-tag)-IE41 protein.

A: analysis by SDS-PAGE;
B: Western blotting;
Mix=solubilized envelope proteins;
C=insoluble proteins;
S=soluble proteins;
L1, L2, L3=fractions recovered in the course of the 3 successive washes;
E1=fraction eliminated by incubation with the Ni-NTA resin;
E2=purified spinach IE41 protein (So)+(His-tag)-IE41.

FIG. 6: the cDNA Encoding the Spinach IE41 Protein.

Figure 7:
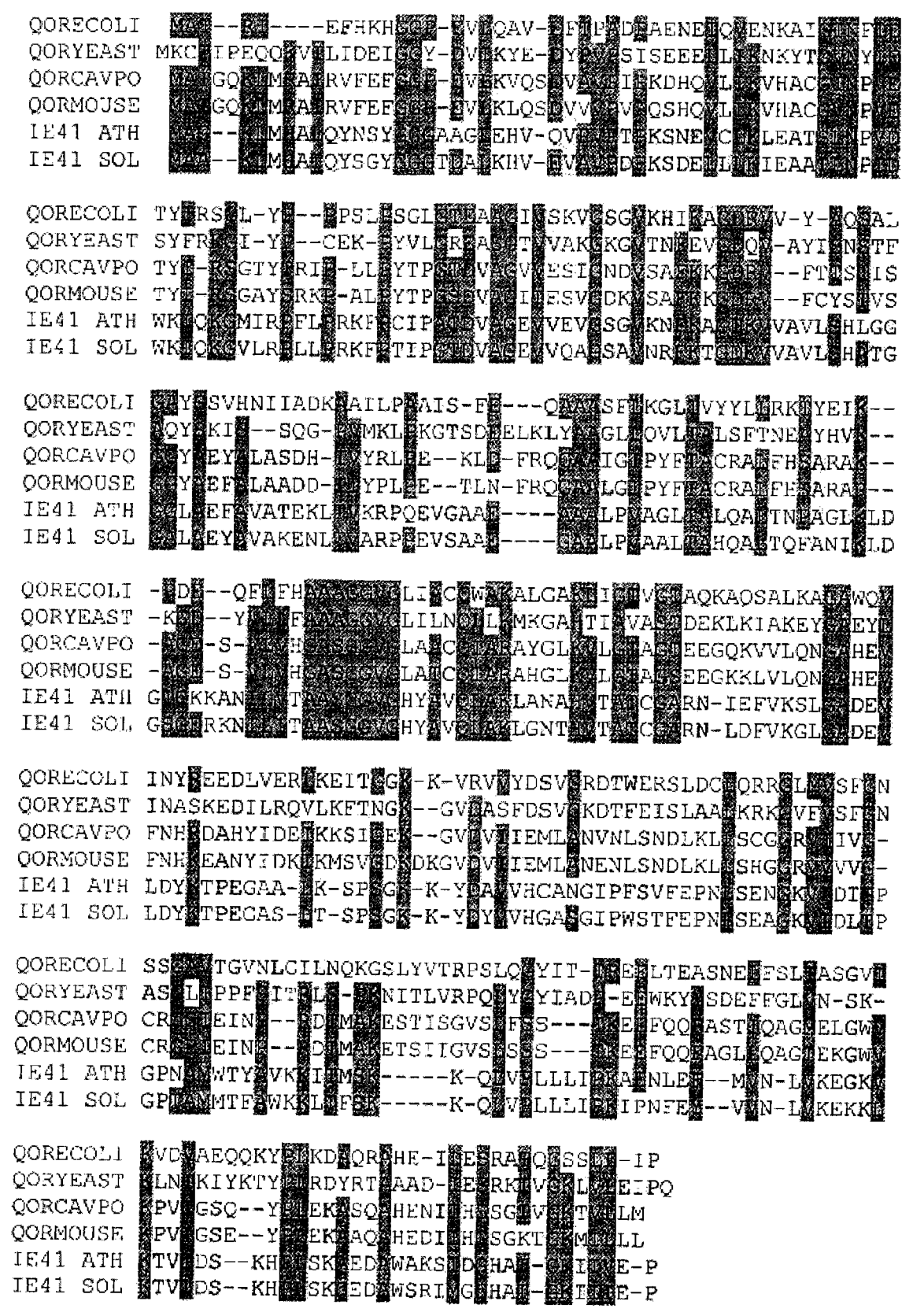

FIG. 7: *Arabidopsis* and spinach IE41 proteins aligned with homologous proteins from a bacterium, from a yeast and from animals. *Arabidopsis thaliana*: IE41 ATH (SEQ ID NO: 1), Spinach: IE41 SOL (SEQ ID NO: 3); *Esherichia coli*: QORECOLI, (SEQ ID NO: 6) *Saccharomyces cerevisiae*: QORYEAST, (SEQ ID NO: 7) *Cavia Porcellus*: QORCAVPO, (SEQ ID NO: 8) Mouse: QORMOUSE. (SEQ ID NO: 9). The residues conserved in the 6 peptide sequences are highlighted in dark gray. The residues conserved in the IE41 sequence and in at least one other homologous protein sequence are highlighted in light gray. The similarities between residues are based on the following groups: ASPTG, ILMV, KRH, NQ, DE, YWF and C.

Figure 8:
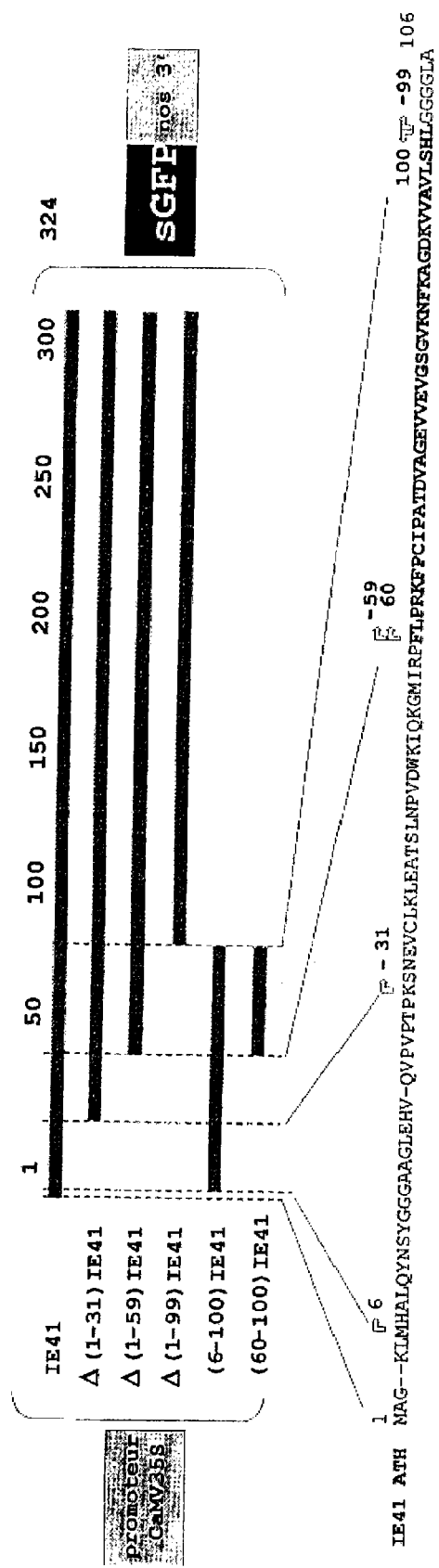

FIG. 8: Constructs used in Example 5, IE41=plasmid 35Ω-IE41-sGFP(S65T); Δ(1-31)IE41=plasmid 35 Ω.- Δ(1-31) IE41-sGFP(S65T); Δ(1-59)IE41=plasmid 35 Ω-Δ(1-59) IE41-sGFP(S65T): Δ(1-99)IE41=plasmid 35 Ω-Δ(1-99) IE41-sGFP(S65T); (6-100)IE41=plasmid 35 Ω-(6-100) IE41-sGFP(S65T); (60-100)IE41=plasmid 35 Ω-(60-100) IE41-sGFP(S65T)

FIG. 9: In Planta Analysis of the Plastid-Targeting of the IE41 Protein. A: SDS-PAGE analysis; B: Western blotting with the anti-GFP antibody: the black arrows indicate the presence of the GFP protein in the fusions expressed in *Arabidopsis*; C: Western blotting with an anti-IE41 antibody: the black arrows indicate the presence of the IE41 protein in the fusions expressed in *Arabidopsis*; the white diamond indicates the position of the natural IE41 protein present in all the extracts; WT=non-transformed plant; M=molecular weight markers; GFP=plasmid 35 Ω-sGFP(S65T); TP GFP=plasmid 35 Ω-TP-sGFP(S65T); IE41 GFP=plasmid 35 Ω-IE41-sGFP (S65T); Δ(1-59)IE41 GFP=plasmid 35 Ω. -Δ.(1-59)IE41-sGFP(S65T); Δ(1-99)IE41 GFP=plasmid 35 Ω-Δ(1-99) IE41-sGFP(S65T); (6-100)IE41 GFP=plasmid 35 Ω-(6-100) IE41-GFP(S65T); (60-100)IE41 GFP=plasmid 35 Ω-(60-l00)IE41-sGFP(S65T).

Figure 10:
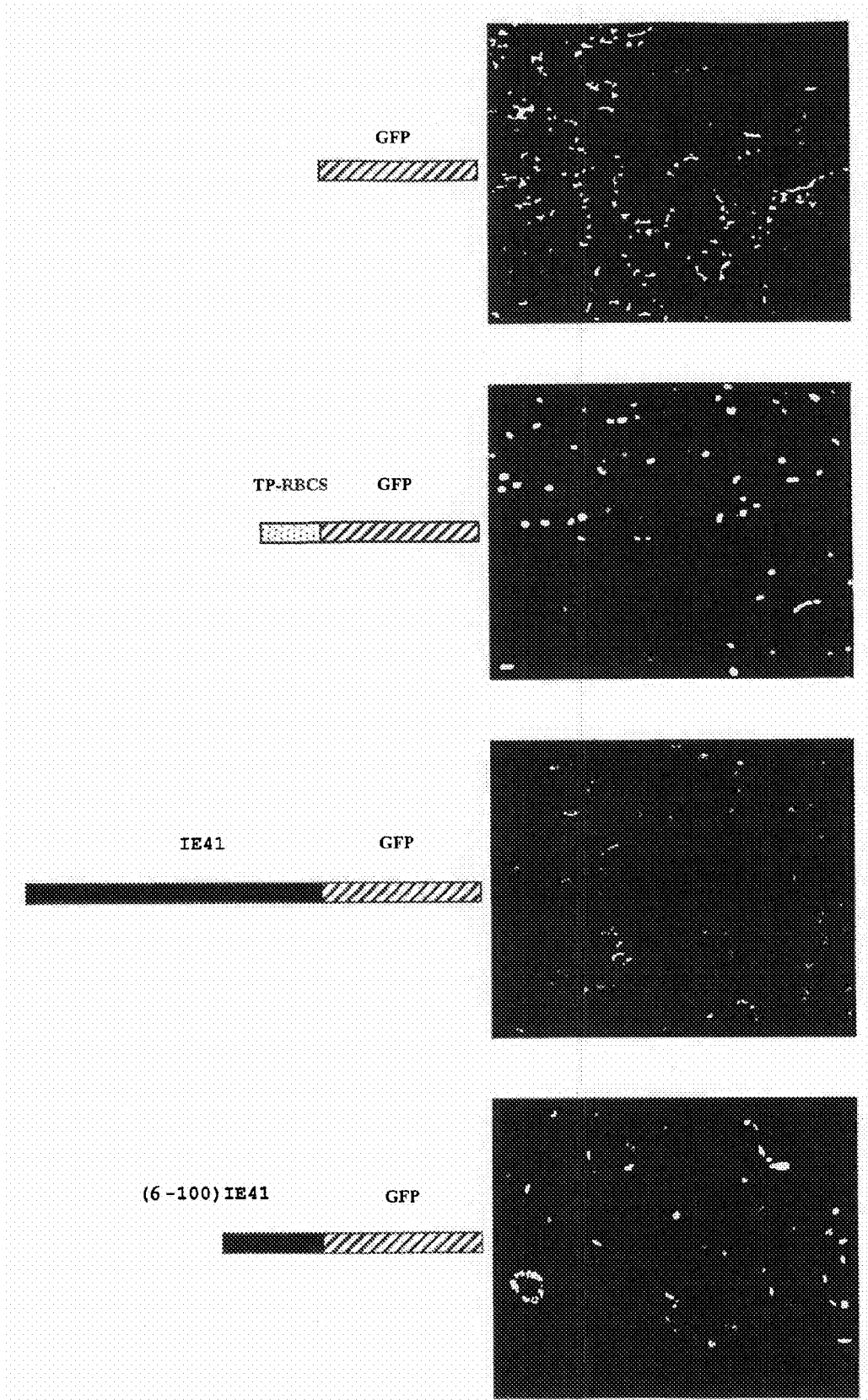

FIG. 10: The subcellular location of the proteins expressed by the various constructs was visualized by fluorescence microscopy, as described in example 5. GFP=plasmid 35 Ω.-sGFP(S65T); TP-RBCS GFP=plasmid 35 Ω-TP-sGFP (S65T); IE41 GFP=plasmid 35.OMEGA.-IE41-sGFP (S65T); (6-100)IE41 GFP=plasmid 35 Ω-(6-100)IE41-sGFP (S65T).

DESCRIPTION OF THE INVENTION

The proteins of the family represented by the 41 kDa *Arabidopsis* protein, and the homologue spinach protein, are referred to hereinafter as IE41 (IE for Inner Envelope according to the nomenclature conventionally used for this membrane system).

The sequence of the *Arabidopsis* IE41 protein is represented in the sequence listing in the appendix under the number SEQ ID NO: 1; the sequence of the cDNA encoding the spinach IE41 protein is represented in the sequence listing in the appendix under the number SEQ ID NO: 2, and the corresponding polypeptide sequence is represented in the sequence listing in the appendix under the number SEQ ID NO: 3.

The inventors investigated which regions of the IE41 proteins were involved in their plastid targeting, and identified a region of 41 amino acids (residues at 60 to 100) that was essential to this targeting.

The sequence of this region is represented in the sequence listing in the appendix under the number SEQ ID NO: 4 for the *Arabidopsis* IE41 protein, and under the number SEQ ID NO: 5 for the spinach IE41 protein.

They also noted that, when fragments of IE41 containing this region were fused to the N-terminal end of a heterologous protein, the recombinant protein resulting from this fusion was targeted to chloroplasts in a manner similar to the whole IE41 protein.

A subject of the present invention is an intraplastid-targeting polypeptide, characterized in that it comprises:

a domain A consisting of a polypeptide having at least 60%, preferably at least 70%, advantageously at least 80%, and entirely preferably at least 90% identity, or at least 65%, preferably at least 75%, advantageously at least 85%, and entirely preferably at least 95% similarity, with one of the polypeptides SEQ ID NO: 4 or SEQ ID NO: 5;

and at least one domain chosen from:

a domain B located at the N-terminal end of domain A, and consisting of a fragment of one of the polypeptides SEQ ID NO: 1 or SEQ ID NO: 3 comprising at least amino acids 49 to 59, preferably at least amino acids 39 to 59, advantageously at least amino acids 29 to 59, entirely preferably at least amino acids 19 to 59, and particularly advantageously at least amino acids 9 to 59 of said polypeptide, or else of a polypeptide having at least 60%, preferably at least 70%, advantageously at least 80%, and entirely preferably at least 90% identity, or at least 65%, preferably at least 75%, advantageously at least 85%, and entirely preferably at least 95% similarity, with said fragment;

a domain C located at the C-terminal end of domain A, and consisting of a fragment of one of the polypeptides SEQ ID NO: 1 or SEQ ID NO: 3 comprising at least amino acids 101 to 111, preferably at least amino acids 101 to 121, advantageously at least amino acids 101 to 131, entirely preferably at least amino acids 101 to 141, and particularly advantageously at least amino acids 101 to 151 of said polypeptide, or else of a polypeptide having at least 60%, preferably at least 70%, advantageously at least 80%, and entirely preferably at least 90% identity, or at least 65%, preferably at least 75%, advantageously at least 85%, and entirely preferably at least 95% similarity, with said fragment.

The percentage identities or the percentage similarities mentioned here are determined by means of the BLASTp software (ALTSCHUL et al., Nucleic Acids Res. 25, 3389-3402, 1997), using the default parameters.

Domains A, B and/or C defined above can come from the same IE41 protein; they can also come from IE41 proteins of different origins.

A subject of the present invention is also any chimeric polypeptide resulting from the fusion of an intraplastid-targeting polypeptide in accordance with the invention with a heterologous polypeptide. Said heterologous polypeptide may be any polypeptide of interest that it is desired to introduce into plants. Preferably, the intraplastid-targeting polypeptide in accordance with the invention is placed at the N-terminal end of the heterologous peptide. It could, however, also be placed within this peptide, or else at its C-terminal end.

A subject of the present invention is also the use of an intraplastid-targeting polypeptide in accordance with the invention, for the importation of a protein of interest into plasts, and advantageously for the targeting of said protein to the inner plastid membrane.

According to a preferred embodiment of the present invention, said intraplastid-targeting polypeptide is used for the importation of said protein of interest into chloroplasts.

In particular, a subject of the present invention is a method for importing a protein of interest into plasts, characterized in that it comprises the expression, in a plant cell containing said plasts, of a chimeric polypeptide resulting from the fusion of an intraplastid-targeting polypeptide in accordance with the invention, with a heterologous polypeptide.

A subject of the present invention is also:

any polynucleotide encoding an intraplastid-targeting polypeptide or a chimeric polypeptide in accordance with the invention;

any recombinant expression cassette comprising a polynucleotide in accordance with the invention placed under the control of suitable sequences for regulating the transcription (in particular transcription promoter and terminator);

any recombinant vector resulting from the insertion, into a suitable host vector, of a polynucleotide or of an expression cassette in accordance with the invention.

A subject of the present invention is also host cells harboring a polynucleotide, an expression cassette or a recombinant vector in accordance with the invention.

The present invention also encompasses transgenic plants genetically transformed with a polynucleotide or an expression cassette in accordance with the invention, and also the progenies of these plants. The invention also comprises the plant cells and tissues, and also the organs or parts of plants, including leaves, stems, roots, flowers, fruits and/or seeds obtained from these plants.

Conventional techniques for constructing recombinant vectors, for transforming host cells or organisms, and for producing recombinant proteins can be used for implementing the present invention.

The choice of the host vector and of the sequences for regulating the expression will be made in particular according to the method of transformation and to the host plant chosen, and/or to the type of cell or of tissue in which it is desired to obtain the expression.

A very large number of promoters that can be used for the expression in plant cells are known in themselves. By way of examples, a constitutive promoter, such as the CaMV 35S promoter or its derivatives, or the promoter of actin or ubiquitin, etc., may be chosen. An inducible promoter or else a tissue-specific promoter may also be chosen, so as to effect the plastid-targeting of the protein of interest only at certain stages of the plant's development, under certain environmental conditions, or in certain target tissues.

For example, if it is desired to preferentially obtain targeting of the protein of interest to chloroplasts, a chimeric polypeptide in accordance with the invention will be expressed under the control of a promoter specific for tissues or organs that are rich in plasts. By way of examples, the promoters of the chlorella virus that regulate expression of the adenine methyltransferase gene (MITRA and HIGGINS, Plant Mol. Biol. 26, 85-93, 1994) or that of the cassava mosaic virus (VERDAGUER et al., Plant Mol. Biol. 37, 1055-1067, 1998) are expressed mainly in the green tissues. The regulatory elements of the promoter of the tomato 2A11 gene allow specific expression in the fruit (VAN HAAREN and HOUCK, Plant Mol. Biol. 17, 615-630, 1991), etc.

Methods for transforming plant cells or whole plants are well known in themselves: by way of nonlimiting examples, mention will be made of the transformation of protoplasts in the presence of polyethylene glycol, electroporation, the use of a particle gun, cytoplasmic or nuclear microinjection, or transformation by means of *Agrobacterium*.

The present invention can be implemented in the usual applications of plast-targeting peptides, and in particular in those mentioned above, so as to act on various plastid functions. This involves, in particular, the modification of functions specific to the inner membrane of the envelope, for example the biosynthesis of pigments, of quinones, of fatty acids, of vitamins and of plant hormone precursors, but also the importation of all the ions and metabolites into the plast.

The characteristics of the plastid-targeting peptides in accordance with the invention, which are very different from those of the known plastid-targeting peptides, make it possible to suppose that the targeting peptides in accordance with the invention use an import system that is different from that involving the TOC and TIC proteins.

As a result of this, the proteins of interest targeted to plasts by means of a targeting peptide in accordance with the invention would not compete with the proteins naturally targeted to the plast by means of the TOC and TIC system, and would not saturate the latter. This would make it possible in particular to prevent leakages into the other subcellular compartments, and to conserve the proteins of interest in the chloroplast, even after several days of expression. This would also make it possible to target to the plasts proteins for which conventional importation by means of an N-terminal cleavable targeting sequence and using the TIC/TOC system would not be functional.

The present invention will be understood more fully from the further description which will follow, which refers to nonlimiting examples illustrating the obtaining and characterization of plastid-targeting peptides in accordance with the invention and their use for the importation of heterologous proteins into chloroplasts.

EXAMPLE 1

Characterization and Cloning of the *Arabidopsis Thaliana* IE41 Protein

In prior studies aimed at identifying the most hydrophobic proteins of spinach chloroplast membrane preparations (SEIGNEURIN-BERNY et al., Plant. J., 19, p.217-228, 1999 ; FERRO et al., Electrophoresis, 21, 3517-3526, 2000), several peptides derived from a 41 kDa protein inhibiting great sequence similarity with a putative protein from *Arabidopsis* (TrEMBL accession number Q9SV68) were demonstrated.

However, analysis of the primary sequence of this 41 kDa protein by means of the TMPred program (HOFMANN and STOFFEL, Biol. Chem. Hoppe-Seyler., 347, 166, 1993), did not make it possible to detect transmembrane segments able to provide anchoring of the protein in a lipid bilayer.

To confirm the location of this protein in the chloroplast envelope, the corresponding cDNA was cloned and the recombinant protein was overexpressed in *E. coli* in order to obtain polyclonal antibodies directed against this protein.

Expression in *E. coli*

The cDNA encoding the 41 kDa *Arabidopsis* protein is obtained by PCR, from an *Arabidopsis* cDNA library, using the following primers:

TCA<u>CATATG</u>GCTGGAAAACTCAATGCAC (SEQ ID NO: 10)

which makes it possible to introduce an NdeI restriction site (underlined) at the 5' end of the cDNA;

ATG<u>GGATCC</u>AACGCTCTTATGGCTCGAC (SEQ ID NO: 11)

which makes it possible to introduce a BamHI restriction site (underlined) at the 3' end of the cDNA.

The amplification fragment is cloned into the plasmid pBluescript KS⁻. The insert is then digested with the NdeI and BamHI restriction enzymes, and inserted into the expression vector pET-15b (NOVAGEN).

The resulting vector allows the expression of a recombinant protein having a polyhistidine extension (His-tag) at its N-terminal end [(His-tag)-P41].

This vector is used for transforming *E. coli* strain BLR (DE3) bacteria.

The recombinant bacteria are cultured in 500 ml of LB medium containing 100 µg/ml of ampicillin at 37° C. When the optical density at 600 nm ($DO_{600}$) of the *E. coli* culture reaches 0.6, IPTG (isopropyl-β-D-galactothiopyranoside) is added at a final concentration of 1 mM so as to induce expression of the 41 kDa protein.

After 3 hours of culture, the cells are centrifuged for 2 min at 13000 rpm (EPPENDORF 5415D).

The pellet is resuspended in 20 ml of lysis buffer (50 mM $NaH_2PO_4$, 300 mM Na Cl, 10 mM imidazole, pH 8) and the bacteria are lysed by sonication (OMRON sonicator, type STP.YM.220.VAC, 6×1 min, 0° C.).

After sonication, the total protein extract is analyzed by SDS 12% PAGE. The gels are stained with Coomassie blue (R-250, BIORAD).

The results are given in FIG. 1A:

Legend of FIG. 1A:
pET-15b=bacteria transformed with the nonrecombinant plasmid (negative control)
pET-15b +insert=bacteria transformed with the recombinant plasmid,
−=no induction with IPTG,
+=induction with IPTG,
*=band corresponding to the recombinant 41 kDa protein.

After induction with IPTG, the recombinant protein is strongly expressed in the bacteria transformed with the plasmid pET-15b containing the *Arabidopsis* cDNA insert.

Solubilization of the Recombinant Protein

The bacterial pellet is suspended in 1 ml of 20 mM Tris/HCl buffer, pH 6.8, and then lysed by sonication (OMRON sonicator, type STP.YM.220.VAC, 6×1 min, 0° C.).

After sonication, a first centrifugation (2 min, 13 000 rpm) of the total protein extract makes it possible to isolate the soluble proteins in the supernatant. The insoluble proteins in the pellet are suspended in 1 ml of a buffer containing detergent (20 mM Tris/HCl pH 6.8, 0.5% Triton X-100). A second centrifugation makes it possible to isolate the membrane proteins solubilized with Triton X-100. The nonsolubilized proteins are resuspended in 20 mM Tris/HCl, pH 6.8 and analyzed. The various fractions are analyzed by SDS-12% PAGE, as indicated above.

The results are given in FIG. 1B:

Legend of FIG. 1B:
pET-15b=bacteria transformed with the nonrecombinant plasmid (negative control), pET-15b + insert=bacteria transformed with the recombinant plasmid,
S=soluble proteins,
D=proteins solubilized in Triton X-100,
I=proteins not solubilized in Triton X-100,
*=band corresponding to the recombinant 41 kDa protein.

It is noted that the recombinant protein (*) is found in 2 different fractions: a water-soluble fraction present in the *E. coli* cytosol and an insoluble fraction, which is not solubilized by Triton X-100, which indicates that it is probably aggregated in the form of inclusion bodies.

Purification of the Recombinant Protein The soluble fraction of the recombinant (His-tag)-P41 protein is purified by affinity chromatography. After centrifugation (10 min at 6000 rpm, EPPENDORF 5415D), the supernatant is loaded onto a 2.5 ml "His-bind resin" affinity column (NOVAGEN) charged with 13 ml of charged buffer (50 mM $NiSO_4$) and equilibrated with 5 ml of equilibrating buffer (20 mM tris/HCl, pH 7.9, 5 mM imidazole, 0.5 M NaCl).

The column is washed with 2 volumes containing 35 mM imidazole, and 2 volumes of lysis buffer containing 60 mM imidazole (L2). The protein is eluted with 6 volumes of lysis buffer containing 250 mM imidazole. The various fractions are analyzed by SDS-12% PAGE and revealed with Coomassie blue.

The results are given in FIG. 2.

Legend of FIG. 2:
C=bacterial pellet diluted in the lysis buffer (10 µl),
S=soluble bacterial proteins (10 µl),
P=proteins not bound (10 µl),
L, L1, L2=washes with the lysis buffer (35 and 60 mM imidazole) (15 µl),
Elution=fraction eluted in the presence of 250 mM imidazole.

Production of Polyclonal Antibodies

The purified recombinant (His-tag)-P41 protein is desalified (SEPHADEX G25 column) and stored at −80° C.

This recombinant protein is used for immunizing rabbits in order to produce polyclonal antibodies directed against the 41 kDa *Arabidopsis* protein.

EXAMPLE 2

Location of the 41 Kda Protein in Chloroplasts

During the purification procedure, the 41 kDa protein behaves like a protein that is water soluble and slightly hydrophobic, which raises the question of its effective association with the chloroplast envelope.

Its subcellular location was therefore verified by analyzing various chloroplast fractions.

Crude chloroplasts are obtained from 3-4 kg of spinach (*Spinacia oleracea* L.) leaves and are purified by isopycnic centrifugation on a Percoll gradient (DOUCE and JOYARD, Methods in chloroplast Molecular Biology. Edelman, M., Hallick, R. and Chua, N.-H., eds. (Amsterdam : Elsevier Science Publishers BV), 239-256, 1982). At this stage, protease inhibitors (1 mM PMSF, 1 mM benzamidine and 0.5 mM aminocaproic acid) are added in order to prevent any protein degradation. The purified chloroplasts are lysed in a hypotonic medium, and the envelope membranes are purified from the lysate by centrifugation on a sucrose gradient (DOUCE and JOYARD, 1982, mentioned above). Envelope subfractions respectively enriched in outer and inner membranes are obtained according to the protocol described by BLOCK et al. (J. Biol. Chem., 258, 13273-13280, 1983).

All the above steps are carried out at between 0 and 5° C. The fractions obtained are stored in liquid nitrogen in 50 mM MOPS-NaOH, pH 7.8, in the presence of protease inhibitors (1 mM benzamidine and 0.5 mM aminocaproic acid).

Analysis Of The Chloroplast Fractions

The SDS-PAGE analyses of the total chloroplasts, or of their envelope membrane, stroma or thylakoid membrane fractions (15 µg), and also of the chloroplast envelope subfractions (15 µg), are carried out as described by CHUA (Methods Enzymol., 69, 434-436, 1980). The resolving and stacking gels (12-15% acrylamide), like the migration buffer, contain 0.1% of SDS. The peptides are revealed either with Coomassie blue (MANIATIS et al., Cold Spring Harbor Laboratory, Cold Spring Harbor, N.Y., 1982) or with silver nitrate (MERRIL et al., Anal. Biochem., 110, 201-207, 1981).

For the Western blotting analyses, the 41 kDa protein is detected using the polyclonal antibodies directed against the recombinant *Arabidopsis* protein produced as described in example 1, labeled with alkaline phosphatase.

The results are given in FIG. 3A.

Legend of FIG. 3A:
C=chloroplast proteins,
E=envelope membrane proteins,
S=stroma proteins,
T=thylakoid membrane proteins.

These results show that the 41 kDa protein is associated only with the chloroplast envelope and is not detected in the stroma or in the thylakoids.

The purified intact chloroplasts are devoid of cytosolic proteins which can contaminate the preparation (DOUCE and JOYARD, 1980, mentioned above). However, the 41 kDa protein could interact specifically with the outer membrane of the chloroplast envelope and could thus be co-purified with the envelope preparations. In order to exclude this possibility, 20 µg of envelope derived from intact chloroplasts are treated with *Bacillus thermoproteolyticus* thermolysin (0, 20, 50 and 100 µg/ml) in order to digest the polypeptides located on the outer surface of the outer membrane of the envelope (JOYARD et al., J. Biol. Chem., 258, 10 000-10 006, 1983). As a control, solubilized envelope proteins are subjected to the same proteolytic treatment.

The presence of the 41 kDa protein is detected by Western blotting, as described above.

The results are given in FIGS. 3B and 3C.

Legend of FIGS. 3B and 3C:
0=absence of thermolysin,
20=thermolysin at 20 µg/ml,
50=thermolysin at 50 µg/ml,
100=thermolysin at 100 µg/ml.

The 41 kDa protein is not affected by the treatment with thermolysin (FIG. 3B), whereas the same proteolytic treatment carried out on solubilized envelope proteins shows the sensitivity of the 41 kDa protein to the thermolysin treatment (FIG. 3C). This result excludes the hypothesis that the 41 kDa protein is located on the outer face of the outer membrane. In fact, the 41 kDa protein is not a cytosolic protein contaminating the chloroplast envelope preparations.

Envelope subfractions respectively enriched in outer and inner membranes are used to specify the sub-location of the 41 kDa protein at the level of the membrane of the chloroplast envelope. The nature of these envelope subfractions was confirmed using the markers IE18 and OEP24, which are respectively intrinsic proteins of the inner and outer membrane of the chloroplast envelope. The IE18 and OEP24 proteins are detected using polyclonal antibodies directed specifically against each of these proteins.

The results are given in FIG. 3D.

Legend of FIG. 3D :
E=envelope membrane proteins,
OM=outer membrane proteins,
IM=inner membrane proteins.

The 41 kDa protein is found, like the IE18 protein, only in the preparations of chloroplast envelopes enriched in inner membrane.

All the results given in FIGS. 3A-3D show that the 41 kDa protein is located at the level of the inner membrane of the chloroplast envelope.

According to conventional nomenclature, this inner envelope protein, which has a theoretical mass by polyacrylamide gel electrophoresis of 41 kDa, is called IE41 (for "Inner Envelope Protein of 41 kDa").

Analysis of the Interactions Between the IE41 Protein and the Inner Membrane of the Chloroplast Envelope In order to analyze more precisely the mode of interaction of the IE41 protein with the chloroplasts inner membrane, various hypotheses were tested:

1) The IE41 protein is a soluble protein located in the intermembrane space between the outer and inner membranes of the chloroplast envelope. This protein would be co-purified with the envelope preparations and sequested in the envelope vesicules. In this case, sonication of the envelope vesicules would make it possible to release IE41.

To test this first hypothesis, envelope proteins (500 µg) are solubilized in 50 mM MOPS, pH 7.8 (500 µl) . The envelope vesicules are sonicated for 10 sec and then centrifuged (20 min at 72 000 g, Beckman L2 65B, SW28 rotor) in order to separate the soluble proteins and the membrane proteins. Each fraction (20 µl) is analyzed by SDS-12% PAGE (visualization: Coomassie blue) and Western blotting.

The results are given in FIG. 4A.

Legend of FIG. 4A:
−=no sonication,
+=sonication,
S=soluble proteins,
I=membrane proteins.

The analyses by SDS-PAGE and Western blotting of the treated envelope fractions show that the IE41 protein is not solubilized after sonication of the envelope vesicules. On the contrary, the major soluble proteins of the stroma (RbcL) which are sequestred in the envelope vesicules, and which are known to contaminate the envelope fractions, are solubilized by this treatment. This shows that the IE41 protein is neither a soluble protein of the intermembrane space, nor a soluble protein of the stroma that contaminates the purified envelope fraction.

2) The IE41 protein may be bound to the inner membrane:
either by anchoring to the lipid bilayer or partial insertion into said bilayer; in this case, only the use of detergent can enable the IE41 protein to be solubilized;
by electrostatic interactions with one or more membrane proteins or the polar surface of the lipid bilayer; in this case, these interactions can be broken, and the IE41 protein can be solubilized by means of an alkaline treatment or by means of high salt concentrations.

In order to determine the type of interactions involved in the binding of IE41 with the inner membrane, the following experiments were carried out:

a) solubilization with Triton X-100:
Envelope vesicules (0.8 mg) are diluted in 1 ml of 50 mM MOPS, pH 7.8, containing 0.05, 0.1 or 0.2% (v/v) of Triton X-100. After incubation for 30 min at 4° C., the mixture is centrifuged in order to separate the soluble proteins and the membrane proteins. All the fractions (20 µl) are analyzed by SDS-12% PAGE (visualization: Coomassie blue) and Western blotting.

The results are given in FIG. 4C.

Legend of FIG. 4C:
Mix=purified envelope vesicules,
M=envelope membrane proteins,
S=envelope soluble proteins.

These results show that the IE41 protein can be completely solubilized with concentrations of Triton X-100 (0.2%) that are much lower than those (of the order of 2%) which are necessary for solubilizing the intrinsic proteins.

b) solubilization by alkaline treatment or by salt treatment.
Purified envelope vesicules (500 µg) are incubated for 30 min at 4° C. in various media (500 µl):
1) 10 mM MOPS, pH 7.8+0.5 M NaCl;
2) 10 mM MOPS, pH 7.8+0.5 M KI;
3) 0.1 M $Na_2CO_3$, pH 11;
4) 0.1 N NaOH,
and then sonicated and centrifuged as described above in order to separate the soluble proteins and the membrane proteins.

All the fractions are analyzed (20 µl) by SDS-12% PAGE (visualization: Coomassie blue) and Western blotting (detection with the polyclonal antibodies directed against the *Arabidopsis* IE41 protein (1/5000 dilution) or directed against the IE18 protein (1/5000 dilution)).

The results are given in FIG. 4B

Legend of FIG. 4B:
+=sonication (10 sec),
NaCl 0.5 M=treatment 1,
KI 0.5 M=treatment 2,
0.1 M $Na_2CO_3$, pH 11=treatment 3,
0.1 N NaOH=treatment 4,
S=soluble protein fraction,
I=insoluble protein fraction.

These results show that the IE41 protein is at least partly solubilized by the salt (KI, NaCl) or moderately alkaline ($Na_2CO_3$) treatments, which have no effect on the intrinsic protein IE18, it only being possible for the latter to be solubilized by a strong alkaline treatment (NaOH).

All the results given in FIGS. 4A, 4B and 4C indicate that the IE41 protein is an extrinsic protein, the binding of which to the inner membrane of the chloroplast envelope involves electrostatic interaction.

EXAMPLE 3

Purification and Characterization of the Spinach IE41 Protein

Surprisingly, the IE41 protein purified from spinach chloroplasts and the recombinant *Arabidopsis* protein have a similar size by SDS-PAGE and Western blotting, which suggest the possibility that IE41 may be targeted to the inner membrane of the envelope without requiring the cleavage of an N-terminal import sequence.

To test this hypothesis, the IE41 protein present in the envelope of spinach chloroplasts was purified in order to sequence it and to compare its sequence with that of the corresponding cDNA.

Immunopurification of the Spinach IE41 Protein

Chloroplast envelope proteins (1 mg) are solubilized in 1 ml of 50 mM Tris/HCl buffer containing 150 mM NaCl and 6 mM CHAPS and centrifuged (20 min, 72 000 g, Beckman L2 65B, SW28 rotor). The soluble proteins are incubated for 1 h at 4° C. with 33 µl of polyclonal serum directed against the recombinant *Arabidopsis* IE41 protein. 50 µg of agarose-protein A (BOEHRINGER) are then added and the mixture is incubated for 3 h at 4° C. After 3 successive washes by centrifugation (EPPENDORF 5415D, 12 000 rpm, 20 min, 4° C.) and resuspension of the pellet in 1 ml of solubilizing buffer (20 mM MOPS, 150 mM NaCl, 6 mM CHAPS, pH 7.8), an excess (50 µg) of recombinant protein (His-tag)-IE41, in 200 µl of solubilizing buffer, is added. The mixture is incubated for 1 h at 4° C., and centrifuged for 20 min at 12 000 rpm (EPPENDORF 5415D). The supernatant is incubated for 1 h with Ni-NTA resin (QIAGEN), pre-equilibrated in the solubilizing buffer, in order to eliminate most of the (His-tag)-IE41 recombinant protein.

Each fraction (20 pl) is analyzed by SDS-126 PAGE (visualization with silver nitrate) and Western blotting (using the rabbit anti-IE41 polyclonal antibodies described in example 1).

The results are given in FIG. 5.

Legend of FIG. 5:
A: analysis by SDS-PAGE;
B: Western blotting;
Mix=solubilized envelope proteins;
C=insoluble proteins;
S=soluble proteins;
L1, L2, L3=fractions recovered in the course of the 3 successive washes;
E1=fraction eliminated by incubation with the Ni-NTA resin;
E2=purified spinach IE41 protein (So) + (His-tag)-IE41.

The E2 fraction comprising the purified natural spinach IE41 protein (So) remains contaminated by the recombinant *Arabidopsis* (His-tag)-IE41 protein.

The difference in size between these two proteins corresponds to the polyhistidine extension (His-tag) present at the N-terminal end of the recombinant protein.

EXAMPLE 4

Obtaining the cDNA Encoding the Spinach IE41 Protein

Partial sequencing of the spinach IE41 protein eluted from the electrophoresis gel made it possible to obtain 9 different peptide sequences. These sequences were used to define degenerate primers which made it possible to isolate the cDNA encoding the IE41 protein.

The complete sequence of this cDNA (SEQ ID No: 2), and also the deduced polypeptide sequence (SEQ ID NO: 3), are given in FIG. 6. The translation initiation codon ATG is indicated in bold letters, and the stop codon TAA is underlined. The 9 peptide sequences obtained by direct sequencing of the spinach IE41 protein are highlighted in gray. The correspondence between the peptides obtained with the sequence deduced from the cDNA of the spinach IE41 protein, in particular in the N-terminal region, and also the presence of a stop codon downstream of the initiating methionine and in the same reading frame, demonstrate that the predicted cDNA is complete and that this protein does not undergo any post-translational maturation during its targeting to the inner membrane of the chloroplast envelope.

The spinach IE41 protein has 75.1% identity and 88.8i similarity with the *Arabidopsis* IE41 protein. This high similarity, and the fact that *Arabidopsis* contains only one ie41 gene per haploid genome, make it possible to conclude that these proteins are encoded by orthologous *Arabidopsis* and spinach genes.

The *Arabidopsis* and spinach IE41 proteins were aligned with homologous proteins from a bacterium, from a yeast and from animals.

The results are given in FIG. 7. *Arabidopsis thaliana*: IE41 ATH (SEQ ID NO: 1), Spinach: IE41 SOL (SEQ ID NO: 3); homologous proteins:
*Esherichia coli*: QORECOLI (SEQ ID NO: 6),
*Saccharomyces cerevisiae*: QORYEAST (SEQ ID NO: 7),
*Cavia Porcellus*: QORCAVPO (SEQ ID NO: 8),
Mouse: QORMOUSE (SEQ ID NO: 9).

The residues conserved in the 6 peptide sequences are highlighted in dark gray. The residues conserved in the IE41 sequence and in at least one other homologous protein sequence are highlighted in light gray. The similarities between residues are based on the following groups: ASPTG, ILMV, KRH, NQ, DE, YWF and C.

The homology searches indicate that the IE41 protein belongs to the dehydrogenase super family, and more particularly to the group of ξ-crystalline-type quinone oxidoreductases (JÖRNVALL et al., FEBS 3, 240-244, 1993). In addition, the sequence comparison between the IE41 proteins and the other proteins of the same family reveals that the first 50 residues in the N-terminal region of these proteins are very conserved between bacteria, plants and animals. This observation suggests that this N-terminal region of the plant IE41 proteins is not involved in targeting into the chloroplast, and is more probably conserved due to the selection pressure exerted during evolution on the catalytic domain of the protein.

EXAMPLE 5

Analysis of the Plastid-Targeting of the *Arabidopsis* IE41 Protein in *Arabidopsis* and Tobacco Cells In order to define the domain essential to the importation of the IE41 protein, various constructs encoding truncated forms of this protein, fused to GFP, are expressed in *Arabidopsis* and tobacco cells.

Construction of the Expression Vectors:

The plasmid [35Ω-sGFP(S65T)] used for these constructs, which comprises the sequence encoding GFP under the control of the 35S promoter, and also the plasmid [35Ω-TP-sGFP (S65T)], which comprises the sequence encoding the targeting peptide (TP) of the ribulose-1,5-bisphosphate carboxylase small subunit, fused to the sequence encoding GFP, were previously described by CHIU et al. (Curr. Biol., 6, 325-330, 1996).

The sequence encoding the *Arabidopsis* IE41 protein is amplified by PCR using the following two primers:

```
XhoI-N-ter
CCTCTCGAGATGGCTGGAAAACTCATGCAC,    (SEQ ID NO: 12)
and

NcoI-C-ter
CAACCCATGGATGGCTCGACAATGATCTTC,    (SEQ ID NO: 13)
``` which introduce, respectively, an XhoI site and an NcoI site (underlined).

The PCR product is cloned, blunt-ended, into the vector pBLUESCRIPT KS (STRATAGENE). The XhoI-NcoI fragment cleaved from the plasmid thus obtained is inserted into the plasmid 35Ω-sGFP(S65T) digested beforehand with SalI-NcoI, in order to create the vector 35Ω-IE41-SGFP(S65T), comprising the coding region of the *Arabidopsis* IE41 protein, fused to GFP. A similar protocol is used for the other constructs:

The sequence encoding the *Arabidopsis* protein lacking the first 31 amino acids is obtained by PCR amplification using the following two primers:

```
    SalI-N-ter
                                         (SEQ ID NO: 14)
    CGGTTGTCGACATGAAGAGTAATGAGGTTTGCCTG NcoI-C-ter
                                         (SEQ ID NO: 13)
    CAACCCATGGATGGCTCGACAATGATCTTC.
```

The plasmid 35Ω-Δ(1-31)IE41-sGFP(S65T) is obtained by insertion of this sequence into the plasmid 35Ω-sGFP(S65T).

The sequence encoding the *Arabidopsis* protein lacking the first 59 amino acids is amplified by PCR using the following two primers:

```
SalI-N-ter
GAATGGTCGACATGTTTCTGCCCCGCAAGTTC,       (SEQ ID NO: 15)
and

NcoI-C-ter
CAACCCATGGATGGCTCGACAATGATCTTC.         (SEQ ID NO: 13)
```

The plasmid 35Ω-Δ(1-59)IE41-sGFP(S65T) is obtained by insertion of this sequence into the plasmid 35Ω-sGFP(S65T).

The sequence encoding the *Arabidopsis* IE41 protein lacking the first 99 amino acids is amplified by PCR using the following two primers:

```
SalI-N-ter
GGTTGTCGACATGCTAGGTGGAGGTGGACTTG        (SEQ ID NO: 16)

NcoI-C-ter
CAACCCATGGATGGCTCGACAATGATCTTC.         (SEQ ID NO: 13)
```

The plasmid 35Ω-Δ(1-99)IE41-sGFP(S65T) is obtained by insertion of this sequence into the plasmid 35Ω-sGFP(S65T).

The sequence encoding the amino acids 6-100 of the *Arabidopsis* IE41 protein is amplified by PCR using the following two primers:

```
XhoI-N-ter
CCTCTCGAGATGGCTGGAAAAACTCATGCAC         (SEQ ID NO: 17)

NcoI-C-ter
ACCCATGGCTAGATGGCTAAGAACCGCTAC.         (SEQ ID NO: 18)
```

The primer SEQ ID NO: 17 comprises an additional nucleotide compared with the primer SEQ ID NO: 15, which creates a reading frame shift in the amplification product, the translation of which begins at the ATG codon corresponding to the methionine at position 6 of the IE41 protein.

The plasmid 35Ω-(6-100)IE41-sGFP(S65T) is obtained by insertion of this sequence into the plasmid 35Ω-sGFP(S65T)

The sequence encoding amino acids 60-100 of the *Arabidopsis* IE41 protein is amplified by PCR using the following two primers:

```
SalI-N-ter
GAATGGTCGACATGTTTCTGCCCCGCAAGTTC        (SEQ ID NO: 15)

NcoI-C-ter
ACCCATGGCTAGATGGCTAAGAACCGCTAC.         (SEQ ID NO: 18)
```

The plasmid 35Ω-(60-100)IE41-sGFP(S65T) is obtained by insertion of this sequence into the plasmid 35Ω-sGFP(S65T).

These various constructs are given in FIG. 8.

Legend of FIG. 8:

IE41=plasmid 35Ω-IE41-sGFP(S65T)
Δ(1-31)IE41=plasmid 35Ω-Δ(1-31)IE41-sGFP(S65T)
Δ(1-59)IE41=plasmid 35Ω-Δ(1-59)IE41-sGFP(S65T)
Δ(1-99)IE41=plasmid 35Ω-Δ(1-99)IE41-sGFP(S65T)
(6-100)IE41=plasmid 35Ω-(6-100)IE41-sGFP(S65T)
(60-100)IE41=plasmid 35Ω-(60-100)IE41-sGFP(S65T)

Bombardment of *Arabidopsis* and Tobacco Cells

The *Arabidopsis* cells are cultured in light for 3 days in GAMBORG's B5 medium (SIGMA, pH 5.8) supplemented with 1.5% sucrose and 1 μM ANA (naphthaleneacetic acid). 15 ml of cell suspension (corresponding to approximately 0.5 g) are transferred into Petri dishes containing the same growth medium to which 0.8% bacto-agar has been added, and incubated for 18-36 h in the light.

BY2 tobacco cells are cultured for 5 days at 27° C. in MURASHIGE and SKOOG medium (MS medium, DUCHEFA, pH 5.8) supplemented with 3% sucrose, 0.2% $KH_2PO_4$, 0.2% myoinositol, 1 μM 2.4D (2.4-dichlorophenoxyacetic acid) and 3 μM thiamine. 2.5 ml of cell suspension (corresponding to approximately 0.3 g) are transferred into Petri dishes containing the same growth medium to which 1% bacto-agar has been added, and are placed at 27° C. for 18-24 h.

The plasmids comprising the test constructs used for the tissue bombardment are prepared using the "QIAfilter Plasmid Midi Kit" (Qiagen, Germany).

The plasmid [35Ω-sGFP(S65T)] (GFP) and the plasmid [35Ω-TP-sGFP(S65T)] (TP-GFP) are respectively used as a negative control and as a positive control.

The plasmids (1 μg) are introduced into the cells using a pneumatic particle gun (PDS-1000/He, BIORAD). The bombardment conditions are as follows: helium pressure of 1350 psi; 1100 psi rupture disks (BIORAD); 10 cm target distance; 1 μm gold microcarriers (BIORAD) are used. After bombardment, the cells are incubated on these same Petri dishes for 18-36 h (in the light for the *Arabidopsis* cells), and then transferred onto glass slides before fluorescence microscopy.

Fluorescence Microscopy

The location of the GFP and of the GFP-fusion peptides in analyzed in the transformed cells by fluorescence microscopy using a ZEISS AXIOPLAN 2 fluorescence microscope and a digital CCD camera (HAMAMATSU). The sets of filters used are: Zeiss filterset 13, 488013-0000 (exciter BP 470/20, beam splitter FT 493, emitter BP 505-530), and Zeiss filter set 15, 488015-0000 (exciter BP 546/12, beam splitter FT 580, emitter LP 590) for the GFP and the chlorophyll autofluorescence, respectively.

Under these conditions, the presence of chlorophyll (specifically located in the chloroplasts) and the location of the GFP in the cell are visualized by virtue of an intense fluorescence.

In the *Arabidopsis* cells transformed with the constructs GFP, Δ(1-99)IE41, and (60-100)IE41, the GFP fluorescence appears to be diffuse and located in the cytosol and the nucleus; no co-localization with chlorophyll is observed.

In the *Arabidopsis* cells transformed with the constructs IE41, Δ(1-31)IE41, Δ(1-59)IE41 and (6-100)IE41, and also with the positive control for localization TP-GFP, a co-localization is, on the other hand observed in the chloroplasts, between the GFP fluorescence and the chlorophyll autofluorescence.

The results are similar in the nonchlorophyll-containing BY2 tobacco cells: the fluorescent labelings observed with the constructs IE41, Δ(1-59)IE41 and (6-100)IE41, and with the positive control for localization TP-GFP, correspond to a plastid localization; on the other hand, the fluorescent labelings observed with the constructs GFP, Δ(1-99)IE41, and (60-100)IE41 correspond to a cytosolic and nuclear localization.

These experiments show that the targeting is also effective in nonchlorophyll-containing plasts.

All the results above show that:
the complete IE41 protein fused to GFP is targeted into the chloroplast;
the 59 residues located at the N-terminal are not essential to the importation;
the 99 residues located at the N-terminal contain a region essential to the importation;
a sequence of 94 residues, corresponding to N-terminal amino acids 6-100, is sufficient to catalyze the importation; the 223 C-terminal residues (101-323) are therefore not essential to the importation.

The internal sequence of 40 amino acids, ranging from residues 60-100, correspond to the domain that is essential for importation. However, this domain, which must be present in order to direct the protein to the plasts, is not sufficient for correct targeting.

EXAMPLE 6

In Planta Analysis of the Plastid-Targeting of the IE41 Protein

The plasmids 35Ω-IE41-sGFP(S65T), 35Ω-Δ(1-31)IE41-sGFP(S65T), 35Ω-Δ(1-59)IE41-sGFP(S65T), 35Ω-Δ(1-99)IE41-sGFP(S65T), 35Ω-(6-100)IE41-sGFP(S65T), and 35Ω-(60-100)IE41-sGFP(S65T), and also the control plasmids 35Ω-sGFP(S65T) and 35Ω-TP-sGFP(S65T), were digested with EcoRI/HindIII in order to recover the expression cassettes.

These cassettes were inserted into the binary plasmid pEL103 (derived from the plasmid pBI121 (AF485783), containing a kanamycin-resistance gene), and the resulting plasmid was used to transform the *Agrobacterium tumefaciens* strain C58 by electroporation. The transformed bacteria were used to transform *Arabidopsis* WS plants by the "floral dip" technique (The Plant Journal 1998; 16: 735-743). The transgenic plants are selected on the basis of their kanamycin resistance.

In order to analyze the expression of the fusion proteins in the transgenic plants, the total proteins are extracted from 10 mg of leaves of each of the tested plants, and solubilized in the following buffer: tetrasodium pyrophosphate (13.4 g/l), Tris-HCl pH 6.8 (50 mM), SDS (1%).

The protein extract is analyzed by SDS-PAGE (12% acrylamide), and by Western blotting using an anti-GFP antibody (antibody 2A5 (Euromedex) diluted 1/4000 in TBST/5% milk; secondary antibody: alkaline phosphatase-conjugated anti-mouse IgG (Promega) diluted 1/10 000 in TBS-Triton), or the rabbit anti-IE41 polyclonal antibodies described in example 1 (diluted 1/5000 in TBS-Triton/5% milk; secondary antibody: alkaline phosphatase-conjugated anti-rabbit IgG (Promega) diluted 1/10 000 in TBS-Triton buffer).

The results of these analyses are illustrated in FIG. 9;

Legend to FIG. 9:
A: SDS-PAGE analysis;
B: Western blotting with the anti-GFP antibody: the black arrows indicate the presence of the GFP protein in the fusions expressed in *Arabidopsis*;
C: Western blotting with an anti-IE41 antibody: the black arrows indicate the presence of the IE41 protein in the fusions expressed in *Arabidopsis*; the white diamond indicates the position of the natural IE41 protein present in all the extracts;
WT=non-transformed plant;
M=molecular weight markers;
GFP=plasmid 35Ω-sGFP(S65T);
TP GFP=plasmid 35Ω-TP-sGFP(S65T);
IE41 GFP=plasmid 35Ω-IE41-sGFP(S65T);
Δ(1-59)IE41 GFP=plasmid 35Ω-Δ(1-59)IE41-sGFP(S65T);
Δ(1-99)IE41 GFP=plasmid 35Ω-Δ(1-99)IE41-sGFP(S65T);
(6-100)IE41 GFP=plasmid 35Ω-(6-100)IE41-sGFP(S65T);
(60-100)IE41 GFP=plasmid 35Ω-(60-100)IE41-sGFP(S65T).

These results show that the fusion proteins are expressed in all the transformed plants.

The subcellular location of the proteins expressed by the various constructs was visualized by fluorescence microscopy, as described in example 5 above.

The results are given in FIG. 10;

Legend of FIG. 10:
GFP=plasmid 35Ω-sGFP(S65T);
TP-RBCS GFP=plasmid 35Ω-TP-sGFP(S65T);
IE41 GFP=plasmid 35Ω-IE41-sGFP(S65T);
(6-100)IE41 GFP=plasmid 35Ω-(6-100)IE41-sGFP(S65T).

It appears that, under the expression conditions used above, it is the N-terminal region of the IE41 protein (residues 6 to 100) which confers the greatest specificity of targeting to the plast. In fact, the construct (6-100)IE41-GFP, which expresses only this region, allows the systematic targeting of all the fluorescence to the plasts. On the other hand, the complete IE41 protein (construct IE41-GFP) induces a less specific plastid-targeting. Under these conditions, the IE41 protein also appears to be targeted to other intracellular compartments.

The invention claimed is:

1. An isolated polynucleotide encoding an intraplastid-targeting polypeptide, wherein the polypeptide consists of:

domain A consisting of: i) amino acids 60-100 of SEQ ID NO: 1; or ii) a fragment of a protein of an inner membrane of a chloroplast envelope, said protein being recognized by an antibody directed against SEQ ID NO: 1, and said fragment having at least 70% identity with amino acids 60-100 of SEQ ID NO: 1 or SEQ ID NO: 3 and when combined with domain B has plastid targeting activity; and a domain B located at the N-terminal end of domain A consisting of iii) a fragment of amino acids 1-59 of SEQ ID NO: 1, said fragment including at least amino acids 49-59 of SEQ ID NO: 1 or SEQ ID NO: 3, or iv) a fragment of a protein of an inner membrane of a chloroplast envelope, said protein being recognized by antibodies directed against the polypeptide SEQ ID NO: 1, and said fragment having at least 60% identity with said fragment iii) and when combined with domain A has plastid targeting activity.

2. The polynucleotide of claim 1, wherein the polypeptide consists of:

domain A consisting of: i) amino acids 60-100 of SEQ ID NO: 1; or ii) a fragment of a protein of an inner membrane of a chloroplast envelope, said protein being recognized by an antibody directed against SEQ ID NO: 1, and said fragment having at least 75% identity with amino acids 60-100 of SEQ ID NO: 1 or SEQ ID NO: 3 and when combined with domain B has plastid targeting activity; and a domain B located at the N-terminal end of domain A consisting of iii) a fragment of amino acids 1-59 of SEQ ID NO: 1, said fragment including at least amino acids 49-59 of SEQ ID NO: 1 or SEQ ID NO: 3, or iv) a fragment of a protein of an inner membrane of a chloroplast envelope, said protein being recognized by antibodies directed against the polypeptide SEQ ID NO: 1, and said fragment having at least 65% identity with said fragment iii) and when combined with domain A has plastid targeting activity.

3. The polynucleotide of claim 1, wherein the polypeptide consists of:

domain A consisting of: i) amino acids 60-100 of SEQ ID NO: 1; or ii) a fragment of a protein of an inner membrane of a chloroplast envelope, said protein being recognized by an antibody directed against SEQ ID NO: 1, and said fragment having at least 85% identity with amino acids 60-100 of SEQ ID NO: 1 or SEQ ID NO: 3 and when combined with domain B has plastid targeting activity; and a domain B located at the N-terminal end of domain A consisting of iii) a fragment of amino acids 1-59 of SEQ ID NO: 1, said fragment including at least amino acids 49-59 of SEQ ID NO: 1 or SEQ ID NO: 3, or iv) a fragment of a protein of an inner membrane of a chloroplast envelope, said protein being recognized by antibodies directed against the polypeptide SEQ ID NO: 1, and said fragment having at least 85% identity with said fragment iii) and when combined with domain A has plastid targeting activity.

4. The polynucleotide of claim 1, wherein the polypeptide consists of:

domain A consisting of: i) amino acids 60-100 of SEQ ID NO: 1; or ii) a fragment of a protein of an inner membrane of a chloroplast envelope, said protein being recognized by an antibody directed against SEQ ID NO: 1, and said fragment having at least 95% identity with amino acids 60-100 of SEQ ID NO: 1 or SEQ ID NO: 3 and when combined with domain B has plastid targeting activity; and a domain B located at the N-terminal end of domain A consisting of iii) a fragment of amino acids 1-59 of SEQ ID NO: 1, said fragment including at least amino acids 49-59 of SEQ ID NO: 1 or SEQ ID NO: 3, or iv) a fragment of a protein of an inner membrane of a chloroplast envelope, said protein being recognized by antibodies directed against the polypeptide SEQ ID NO: 1, and said fragment having at least 95% identity with said fragment iii) and when combined with domain A has plastid targeting activity.

5. The polynucleotide of claim 1, wherein domain B consists of amino acids 39-59 of SEQ ID NO: 1 or SEQ ID NO: 3, or a fragment of a protein of the inner membrane of the chloroplast envelope, said protein being recognized by antibodies directed against the polypeptide SEQ ID NO: 1, and said fragment having at least 60% identity with amino acids 39-59 of SEQ ID NO: 1.

6. The polynucleotide of claim 5, wherein domain B consists of amino acids 29-59 of SEQ ID NO: 1, or a fragment of a protein of the inner membrane of the chloroplast envelope, said protein being recognized by antibodies directed against the polypeptide SEQ ID NO: 1, and said fragment having at least 60% identity with amino acids 29-59 of SEQ ID NO: 1.

7. The polynucleotide of claim 6, wherein domain B consists of amino acids 19-59 of SEQ ID NO: 1, or a fragment of a protein of the inner membrane of the chloroplast envelope, said protein being recognized by antibodies directed against the polypeptide SEQ ID NO: 1, and said fragment having at least 60% identity with amino acids 19-59 of SEQ ID NO: 1.

8. The polynucleotide of claim 7, wherein domain B consists of amino acids 9-59 of SEQ ID NO: 1, or a fragment of a protein of the inner membrane of the chloroplast envelope, said protein being recognized by antibodies directed against the polypeptide SEQ ID NO: 1, and said fragment having at least 60% identity with amino acids 9-59 of SEQ ID NO: 1.

9. The polynucleotide of claim 8, wherein domain B consists of amino acids 6-59 of SEQ ID NO: 1, or of a fragment of a protein of the inner membrane of the chloroplast envelope, said protein being recognized by antibodies directed against the polypeptide SEQ ID NO: 1, and said fragment having at least 60% identity with amino acids 6-59 of SEQ ID NO: 1.

10. The polynucleotide of claim 9, wherein domain A consists of amino acids 60-100 of SEQ ID NO: 1, or of a fragment of a protein of the inner membrane of the chloroplast envelope, said protein being recognized by antibodies directed against the polypeptide SEQ ID NO: 1, and said fragment having at least 70% identity with amino acids 60-100 of SEQ ID NO: 1.

11. An expression cassette comprising the polynucleotide of claim 1, placed under the control of sequences regulating the expression of the polynucleotide.

12. A recombinant vector comprising the polynucleotide of claim 1.

13. A recombinant vector comprising the expression cassette of claim 11.

14. A method of producing an intraplastid-targeting polypeptide, comprising expressing the polynucleotide of claim 1.

15. A method of producing an intraplastid-targeting polypeptide, comprising expressing the expression cassette of claim 11 in a host cell.

16. A method of producing an intraplastid-targeting polypeptide, comprising expressing the recombinant vector of claim 12 in a host cell.

17. A method of producing an intraplastid-targeting polypeptide, comprising expressing the recombinant vector of claim 13 in a host cell.

* * * * *

SEQUENCE LISTING

<160> NUMBER OF SEQ ID NOS: 18

<210> SEQ ID NO 1
<211> LENGTH: 329
<212> TYPE: PRT
<213> ORGANISM: Arabidopsis thaliana

<400> SEQUENCE: 1

Met Ala Gly Lys Leu Met His Ala Leu Gln Tyr Asn Ser Tyr Gly Gly
1               5                   10                  15

Gly Ala Ala Gly Leu Glu His Val Gln Val Pro Val Pro Thr Pro Lys
            20                  25                  30

Ser Asn Glu Val Cys Leu Lys Leu Glu Ala Thr Ser Leu Asn Pro Val
        35                  40                  45

Asp Trp Lys Ile Gln Lys Gly Met Ile Arg Pro Phe Leu Pro Arg Lys
    50                  55                  60

Phe Pro Cys Ile Pro Ala Thr Asp Val Ala Gly Glu Val Val Glu Val
65                  70                  75                  80

Gly Ser Gly Val Lys Asn Phe Lys Ala Gly Asp Lys Val Val Ala Val
                85                  90                  95

Leu Ser His Leu Gly Gly Gly Leu Ala Glu Phe Ala Val Ala Thr
            100                 105                 110

Glu Lys Leu Thr Val Lys Arg Pro Gln Glu Val Gly Ala Ala Glu Ala
            115                 120                 125

Ala Ala Leu Pro Val Ala Gly Leu Thr Ala Leu Gln Ala Leu Thr Asn
    130                 135                 140

Pro Ala Gly Leu Lys Leu Asp Gly Thr Gly Lys Lys Ala Asn Ile Leu
145                 150                 155                 160

Val Thr Ala Ala Ser Gly Gly Val Gly His Tyr Ala Val Gln Leu Ala
                165                 170                 175

Lys Leu Ala Asn Ala His Val Thr Ala Thr Cys Gly Ala Arg Asn Ile
            180                 185                 190

Glu Phe Val Lys Ser Leu Gly Ala Asp Glu Val Leu Asp Tyr Lys Thr
            195                 200                 205

Pro Glu Gly Ala Ala Leu Lys Ser Pro Ser Gly Lys Lys Tyr Asp Ala
    210                 215                 220

Val His Cys Ala Asn Gly Ile Pro Phe Ser Val Phe Glu Pro Asn
225                 230                 235                 240

Leu Ser Glu Asn Gly Lys Val Ile Asp Ile Thr Pro Gly Pro Asn Ala
                245                 250                 255

Met Trp Thr Tyr Ala Val Lys Lys Ile Thr Met Ser Lys Lys Gln Leu
            260                 265                 270

Val Pro Leu Leu Leu Ile Pro Lys Ala Glu Asn Leu Glu Phe Met Val
            275                 280                 285

Asn Leu Val Lys Glu Gly Lys Val Lys Thr Val Ile Asp Ser Lys His
    290                 295                 300

Pro Leu Ser Lys Ala Glu Asp Ala Trp Ala Lys Ser Ile Asp Gly His
305                 310                 315                 320

Ala Thr Gly Lys Ile Ile Val Glu Pro
                325

<210> SEQ ID NO 2
<211> LENGTH: 960
<212> TYPE: DNA

<213> ORGANISM: Spinacia oleracea

<400> SEQUENCE: 2

```
ccatcctaat acgactcact atagggctcg agcggccgcc cgggcaggtc aaactgtggt      60
aagataatac agtaccatta ccatctgacg cgcaaatggc tgctaagcta atgcatgcga     120
ttcaatattc tggctatggt ggtggaactg atgctttaaa gcatgttgaa gttgctgttc     180
ctgatccaaa gtctgatgag ttattgctta aaattgaggc tgcaactttg aacccaattg     240
attggaagat tcagaagggt gtacttcgtc ccctcttacc ccgcaagttc cctactatac     300
ctggaactga tgttgctggg gaggtagtcc aggctggatc tgctgtaaat aggtttaaaa     360
ctggtgacaa agtcgtggcc gtgcttagtc atgctactgg gggtgcacta gctgaatatg     420
ccgtggcgaa ggagaacctg acagttgcta gaccaccaga agtatcagca gcagaaggtg     480
ctgccttacc tgttgctgcc ctcacggctc accaagctct cacccagttt gccaacatca     540
agctcgatgg aagtggtgaa aggaagaaca tattgatcac ggctgcatca gggggtgtgg     600
gccactatgc ggtccagctg caaagctcg ggaacacgca tgtaacagca acatgtggag     660
cccgcaacct agatttcgtg aaaggcttgg gtgccgatga ggttcttgac tacaaaacac     720
ctgaaggggc gtccttgaca agcccgtcag gaaagaaata tgactacgta gtccacggtg     780
caagcggaat cccttggtcc acctttgagc ccaatttgag tgaagcaggt aaggtaatag     840
atttgactcc tggcccaact gcaatgatga catttgcttg gaaaaagcta acattctcca     900
aaaagcagct ggtgcctctg cttttgatac caaagatccc caactttgaa tatgttgtga     960
```

<210> SEQ ID NO 3
<211> LENGTH: 329
<212> TYPE: PRT
<213> ORGANISM: Spinacia oleracea

<400> SEQUENCE: 3

```
Met Ala Ala Lys Leu Met His Ala Ile Gln Tyr Ser Gly Tyr Gly Gly
1               5                   10                  15

Gly Thr Asp Ala Leu Lys His Val Glu Val Ala Val Pro Asp Pro Lys
            20                  25                  30

Ser Asp Glu Leu Leu Lys Ile Glu Ala Ala Thr Leu Asn Pro Ile
        35                  40                  45

Asp Trp Lys Ile Gln Lys Gly Val Leu Arg Pro Leu Leu Pro Arg Lys
    50                  55                  60

Phe Pro Thr Ile Pro Gly Thr Asp Val Ala Gly Glu Val Val Gln Ala
65                  70                  75                  80

Gly Ser Ala Val Asn Arg Phe Lys Thr Gly Asp Lys Val Val Ala Val
                85                  90                  95

Leu Ser His Ala Thr Gly Gly Ala Leu Ala Glu Tyr Ala Val Ala Lys
            100                 105                 110

Glu Asn Leu Thr Val Ala Arg Pro Pro Glu Val Ser Ala Ala Glu Gly
        115                 120                 125

Ala Ala Leu Pro Val Ala Ala Leu Thr Ala His Gln Ala Leu Thr Gln
    130                 135                 140

Phe Ala Asn Ile Lys Leu Asp Gly Ser Gly Glu Arg Lys Asn Ile Leu
145                 150                 155                 160

Ile Thr Ala Ala Ser Gly Gly Val Gly His Tyr Ala Val Gln Leu Ala
                165                 170                 175

Lys Leu Gly Asn Thr His Val Thr Ala Thr Cys Gly Ala Arg Asn Leu
            180                 185                 190
```

```
Asp Phe Val Lys Gly Leu Gly Ala Asp Glu Val Leu Asp Tyr Lys Thr
            195                 200                 205

Pro Glu Gly Ala Ser Leu Thr Ser Pro Ser Gly Lys Lys Tyr Asp Tyr
        210                 215                 220

Val Val His Gly Ala Ser Gly Ile Pro Trp Ser Thr Phe Glu Pro Asn
225                 230                 235                 240

Leu Ser Glu Ala Gly Lys Val Ile Asp Leu Thr Pro Gly Pro Thr Ala
            245                 250                 255

Met Met Thr Phe Ala Trp Lys Lys Leu Thr Phe Ser Lys Lys Gln Leu
        260                 265                 270

Val Pro Leu Leu Ile Pro Lys Ile Pro Asn Phe Glu Tyr Val Val
        275                 280                 285

Asn Leu Val Lys Glu Lys Lys Leu Lys Thr Val Ile Asp Ser Lys His
            290                 295                 300

Pro Leu Ser Lys Gly Glu Asp Ala Trp Ser Arg Ile Met Gly Gly His
305                 310                 315                 320

Ala Thr Gly Lys Ile Ile Ile Glu Pro
            325

<210> SEQ ID NO 4
<211> LENGTH: 61
<212> TYPE: PRT
<213> ORGANISM: Arabidopsis thaliana

<400> SEQUENCE: 4

Leu Glu Ala Thr Ser Leu Asn Pro Val Asp Trp Lys Ile Gln Lys Gly
1               5                   10                  15

Met Ile Arg Pro Phe Leu Pro Arg Lys Phe Pro Cys Ile Pro Ala Thr
            20                  25                  30

Asp Val Ala Gly Glu Val Val Glu Val Gly Ser Gly Val Lys Asn Phe
        35                  40                  45

Lys Ala Gly Asp Lys Val Val Ala Val Leu Ser His Leu
    50                  55                  60

<210> SEQ ID NO 5
<211> LENGTH: 61
<212> TYPE: PRT
<213> ORGANISM: Spinacia oleracea

<400> SEQUENCE: 5

Ile Glu Ala Ala Thr Leu Asn Pro Ile Asp Trp Lys Ile Gln Lys Gly
1               5                   10                  15

Val Leu Arg Pro Leu Leu Pro Arg Lys Phe Pro Thr Ile Pro Gly Thr
            20                  25                  30

Asp Val Ala Gly Glu Val Val Gln Ala Gly Ser Ala Val Asn Arg Phe
        35                  40                  45

Lys Thr Gly Asp Lys Val Val Ala Val Leu Ser His Ala
    50                  55                  60

<210> SEQ ID NO 6
<211> LENGTH: 288
<212> TYPE: PRT
<213> ORGANISM: Escherichia coli

<400> SEQUENCE: 6

Met Ala Thr Arg Ile Glu Phe His Lys His Gly Gly Pro Glu Val Leu
1               5                   10                  15
```

```
Gln Ala Val Glu Phe Thr Pro Ala Asp Pro Ala Glu Asn Glu Ile Gln
             20                  25                  30

Val Glu Asn Lys Ala Ile Gly Ile Asn Phe Ile Asp Thr Tyr Ile Arg
         35                  40                  45

Ser Gly Leu Tyr Pro Pro Ser Leu Pro Ser Gly Leu Gly Thr Glu
     50                  55                  60

Ala Ala Gly Ile Val Ser Lys Val Gly Ser Gly Val Lys His Ile Lys
 65                  70                  75                  80

Ala Gly Asp Arg Val Val Tyr Ala Gln Ser Ala Leu Gly Ala Tyr Ser
                 85                  90                  95

Ser Val His Asn Ile Ile Ala Asp Lys Ala Ala Ile Leu Pro Ala Ala
                100                 105                 110

Ile Ser Phe Glu Gln Ala Ala Ser Phe Leu Lys Gly Leu Thr Val
            115                 120                 125

Tyr Tyr Leu Leu Arg Lys Thr Tyr Glu Ile Lys Pro Asp Glu Gln Phe
        130                 135                 140

Leu Phe His Ala Ala Gly Gly Val Gly Leu Ile Ala Cys Gln Trp
145                 150                 155                 160

Ala Lys Ala Leu Gly Ala Lys Leu Ile Gly Thr Val Gly Thr Ala Gln
                165                 170                 175

Lys Ala Gln Ser Ala Leu Lys Ala Gly Ala Trp Gln Val Ile Asn Tyr
            180                 185                 190

Arg Glu Glu Asp Leu Val Glu Arg Leu Lys Glu Ile Thr Gly Gly Lys
        195                 200                 205

Lys Val Arg Val Val Tyr Asp Ser Val Gly Arg Asp Thr Trp Glu Arg
    210                 215                 220

Ser Leu Asp Cys Leu Gln Arg Arg Gly Leu Met Val Ser Phe Gly Asn
225                 230                 235                 240

Ser Ser Gly Ala Val Thr Gly Val Asn Leu Gly Ile Leu Asn Gln Lys
                245                 250                 255

Gly Ser Leu Tyr Val Thr Arg Pro Ser Leu Gln Gly Tyr Ile Thr Thr
            260                 265                 270

Arg Glu Glu Leu Thr Glu Ala Ser Asn Glu Leu Phe Ser Leu Ile Ala
        275                 280                 285

<210> SEQ ID NO 7
<211> LENGTH: 334
<212> TYPE: PRT
<213> ORGANISM: Saccharomyces cerevisiae

<400> SEQUENCE: 7

Met Lys Cys Thr Ile Pro Glu Gln Gln Lys Val Ile Leu Ile Asp Glu
1               5                   10                  15

Ile Gly Gly Tyr Asp Val Ile Lys Tyr Glu Asp Tyr Pro Val Pro Ser
            20                  25                  30

Ile Ser Glu Glu Glu Leu Leu Ile Lys Asn Lys Tyr Thr Gly Val Asn
        35                  40                  45

Tyr Ile Glu Ser Tyr Phe Arg Lys Gly Ile Tyr Pro Cys Glu Lys Pro
    50                  55                  60

Tyr Val Leu Gly Arg Glu Ala Ser Gly Thr Val Val Ala Lys Gly Lys
65                  70                  75                  80

Gly Val Thr Asn Phe Glu Val Gly Asp Gln Val Ala Tyr Ile Ser Asn
                85                  90                  95

Ser Thr Phe Ala Gln Tyr Ser Lys Ile Ser Ser Gln Gly Pro Val Met
            100                 105                 110
```

-continued

```
Lys Leu Pro Lys Gly Thr Ser Asp Glu Glu Leu Lys Leu Tyr Ala Ala
            115                 120                 125

Gly Leu Gln Val Leu Thr Ala Leu Ser Phe Thr Asn Glu Ala Tyr
    130                 135                 140

His Val Lys Lys Gly Asp Tyr Val Leu Leu Phe Ala Ala Ala Gly Gly
145                 150                 155                 160

Val Gly Leu Ile Leu Asn Gln Leu Leu Lys Met Lys Gly Ala His Thr
                165                 170                 175

Ile Ala Val Ala Ser Thr Asp Glu Lys Leu Lys Ile Ala Lys Glu Tyr
            180                 185                 190

Gly Ala Glu Tyr Leu Ile Asn Ala Ser Lys Glu Asp Ile Leu Arg Gln
        195                 200                 205

Val Leu Lys Phe Thr Asn Gly Lys Gly Val Asp Ala Ser Phe Asp Ser
    210                 215                 220

Val Gly Lys Asp Thr Phe Glu Ile Ser Leu Ala Ala Leu Lys Arg Lys
225                 230                 235                 240

Gly Val Phe Val Ser Phe Gly Asn Ala Ser Gly Leu Ile Pro Pro Phe
                245                 250                 255

Ser Ile Thr Arg Leu Ser Pro Lys Asn Ile Thr Leu Val Arg Pro Gln
            260                 265                 270

Leu Tyr Gly Tyr Ile Ala Asp Pro Glu Glu Trp Lys Tyr Tyr Ser Asp
        275                 280                 285

Glu Phe Phe Gly Leu Val Asn Ser Lys Lys Leu Asn Ile Lys Ile Tyr
    290                 295                 300

Lys Thr Tyr Pro Leu Arg Asp Tyr Arg Thr Ala Ala Ala Asp Ile Glu
305                 310                 315                 320

Ser Arg Lys Thr Val Gly Lys Leu Val Leu Glu Ile Pro Gln
                325                 330

<210> SEQ ID NO 8
<211> LENGTH: 192
<212> TYPE: PRT
<213> ORGANISM: Cavia porcellus

<400> SEQUENCE: 8

Met Ala Thr Gly Gln Lys Leu Met Arg Ala Ile Arg Val Phe Glu Phe
1               5                   10                  15

Gly Gly Pro Glu Val Leu Lys Val Gln Ser Asp Val Ala Val Pro Ile
            20                  25                  30

Pro Lys Asp His Gln Val Leu Ile Lys Val His Ala Cys Gly Ile Asn
        35                  40                  45

Pro Val Glu Thr Tyr Ile Arg Ser Gly Thr Tyr Thr Arg Ile Pro Leu
    50                  55                  60

Leu Pro Tyr Thr Pro Gly Thr Asp Val Ala Gly Val Val Glu Ser Ile
65                  70                  75                  80

Gly Asn Asp Val Ser Ala Phe Lys Lys Gly Asp Arg Val Phe Thr Thr
                85                  90                  95

Ser Thr Ile Ser Gly Gly Tyr Ala Glu Tyr Ala Leu Ala Ser Asp His
            100                 105                 110

Thr Val Tyr Arg Leu Pro Glu Lys Leu Asp Phe Arg Gln Gly Ala Ala
        115                 120                 125

Ile Gly Ile Pro Tyr Phe Thr Ala Cys Arg Ala Leu Phe His Ser Ala
    130                 135                 140

Arg Ala Lys Ala Gly Glu Ser Val Leu Val His Gly Ala Ser Gly Gly
```

```
                145                 150                 155                 160
Val Gly Leu Ala Ala Cys Gln Ile Ala Arg Ala Tyr Gly Leu Lys Val
                165                 170                 175
Leu Gly Thr Ala Gly Thr Glu Glu Gly Gln Lys Val Val Leu Gln Asn
                180                 185                 190

<210> SEQ ID NO 9
<211> LENGTH: 331
<212> TYPE: PRT
<213> ORGANISM: Mus musculus

<400> SEQUENCE: 9

Met Ala Thr Gly Gln Lys Leu Met Arg Ala Ile Arg Val Phe Glu Phe
1               5                   10                  15
Gly Gly Pro Glu Val Leu Lys Leu Gln Ser Asp Val Val Pro Val
                20                  25                  30
Pro Gln Ser His Gln Val Leu Ile Lys Val His Ala Cys Gly Val Asn
                35                  40                  45
Pro Val Glu Thr Tyr Ile Arg Ser Gly Ala Tyr Ser Arg Lys Pro Ala
            50                  55                  60
Leu Pro Tyr Thr Pro Gly Ser Asp Val Ala Gly Ile Ile Glu Ser Val
65                  70                  75                  80
Gly Asp Lys Val Ser Ala Phe Lys Lys Gly Asp Arg Val Phe Cys Tyr
                85                  90                  95
Ser Thr Val Ser Gly Gly Tyr Ala Glu Phe Ala Leu Ala Ala Asp Asp
                100                 105                 110
Thr Ile Tyr Pro Leu Pro Glu Thr Leu Asn Phe Arg Gln Gly Ala Ala
                115                 120                 125
Leu Gly Ile Pro Tyr Phe Thr Ala Cys Arg Ala Leu Phe His Ser Ala
            130                 135                 140
Arg Ala Arg Ala Gly Glu Ser Val Leu Val His Gly Ala Ser Gly Gly
145                 150                 155                 160
Val Gly Leu Ala Thr Cys Gln Ile Ala Arg Ala His Gly Leu Lys Val
                165                 170                 175
Leu Gly Thr Ala Gly Ser Glu Glu Gly Lys Lys Leu Val Leu Gln Asn
                180                 185                 190
Gly Ala His Glu Val Phe Asn His Lys Glu Ala Asn Tyr Ile Asp Lys
                195                 200                 205
Ile Lys Met Ser Val Gly Asp Lys Asp Lys Gly Val Asp Val Ile Ile
            210                 215                 220
Glu Met Leu Ala Asn Glu Asn Leu Ser Asn Asp Leu Lys Leu Leu Ser
225                 230                 235                 240
His Gly Gly Arg Val Val Val Gly Cys Arg Gly Pro Ile Glu Ile
                245                 250                 255
Asn Pro Arg Asp Thr Met Ala Lys Glu Thr Ser Ile Ile Gly Val Ser
            260                 265                 270
Leu Ser Ser Ser Thr Lys Glu Glu Phe Gln Gln Phe Ala Gly Leu Leu
                275                 280                 285
Gln Ala Gly Ile Glu Lys Gly Trp Val Lys Pro Val Ile Gly Ser Glu
                290                 295                 300
Tyr Pro Leu Glu Lys Ala Ala Gln Ala His Glu Asp Ile Ile His Gly
305                 310                 315                 320
Ser Gly Lys Thr Gly Lys Met Ile Leu Leu Leu
                325                 330
```

<210> SEQ ID NO 10
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 10
tcacatatgg ctggaaaact caatgcac					28

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 11
arggatccac gctcttatgg ctcgac					26

<210> SEQ ID NO 12
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 12
cctctcgaga tggctggaaa actcatgcac					30

<210> SEQ ID NO 13
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 13
caacccatgg atggctcgac aatgatcttc					30

<210> SEQ ID NO 14
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 14
cggttgtcga catgaagagt aatgaggttt gccth					35

<210> SEQ ID NO 15
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 15
gaatggtcga catgtttctg ccccgcaagt tc					32

<210> SEQ ID NO 16
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 16
ggttgtcgac atgctaggtg gaggtggact tg                            32

<210> SEQ ID NO 17
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 17
cctctcgaga tggctggaaa aactcatgca c                             31

<210> SEQ ID NO 18
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 18
acccatggct agatggctaa gaaccgctac                               30
```